United States Patent [19]

Polt

[11] Patent Number: 5,470,949
[45] Date of Patent: Nov. 28, 1995

[54] METHOD FOR MAKING AMINO ACID GLYCOSIDES AND GLYCOPEPTIDES

[75] Inventor: Robin L. Polt, Tucson, Ariz.

[73] Assignee: The Arizona Board of Regents on Behalf of the University of Arizona, Tucson, Ariz.

[21] Appl. No.: 990,960

[22] Filed: Dec. 15, 1992

[51] Int. Cl.$^6$ .............................. A61K 38/00; C07K 5/00; C07K 7/00; C07K 17/00
[52] U.S. Cl. .................... 530/322; 530/327; 530/328; 530/329; 530/330; 530/331; 564/197; 564/165; 562/575
[58] Field of Search ...................... 530/322, 331, 530/327, 328, 329, 330; 514/19; 564/197, 165; 562/575

[56] References Cited

U.S. PATENT DOCUMENTS 4,518,711  5/1985  Hruby et al. ............................. 514/11

OTHER PUBLICATIONS

Bodor, et al., "A Strategy for Delivering Peptides into the Central Nervous System by Sequential Metabolism," *Science*, vol. 257:1698–1700 (1992).

Borman, Stu, "Blood–Brain Barrier Bridged by Molecular Packaging Technique," *C&EN*, pp. 57–58 (Oct. 5, 1992).

Polt, Et Al., "General Methods for Alpha– or Beta–O–Ser/Thr Glycosides and Glycopeptides. Solid Phase Synthesis of O–Glycosyl Cyclic Enkephalin Analogs," *ACS Journal* published Dec. 16, 1992.

Szabo, et al., "O–Glycopeptides: A Simple beta–Stereoselective Glycosidation of Serine and Threonine Via A Favorable Hydrogen Bonding Pattern," *Tetrahedron Letters*, 32:58 (1991).

Polt, et al., "Alpha– and Beta–O–Glycosides via Nucleophilic Activation by Hydrogen Bond Acceptors. New Synthetic Methods for O–Linked Glycopeptides and Glycosphingolipids," American Chemical Society Abstract, published Mar. 2, 1992.

*Primary Examiner*—Jill Warden
*Assistant Examiner*—Sheela J. Huff
*Attorney, Agent, or Firm*—Quarles & Brady

[57] ABSTRACT

A compound of the formula

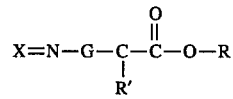

is disclosed. X is selected from the group consisting of aryl, alkyl, imidate ester, imino ester, amidine, azide, isocyanate, and dithiocarbonate. R' is a group selected from the group consisting of groups containing a hydroxyl moiety, groups containing a protected hydroxyl moiety, and groups containing an O-linked sugar. G is a carbon chain of 0–10 carbons and R is not a methyl group and is a group capable of removal under conditions compatible with glycopeptide synthesis. In a preferred form the compound, R is selected from the group consisting of benzylic or allyl groups and X is $CPh_2$. A method of forming a glycocide from the compound is also disclosed.

3 Claims, 12 Drawing Sheets unfavorable H-bond          favorable H-bond

FIG 3

Table 1  $^1$H-NMR data for glycosides[a]

Chemical shifts (p.p.m.)                Coupling constants (Hz)

| Number | 8 | 11 | 13 | $^J$H,H | 8 | 11 | 13 |
|---|---|---|---|---|---|---|---|
| H-1    | 4.58 | 4.53 | 4.64 | 1,2    | 7.6  | 7.5  | 7.6  |
| H-2    | 4.85 | 4.83 | 4.83 | 2,3    | 9.1  | 8.9  | 9.1  |
| H-3    | 5.16 | 5.10 | 5.14 | 3,4    | 9.1  | 8.8  | 9.1  |
| H-4    | 3.73 | 3.76 | 3.72 | 4,5    | 8.9  | 8.4  | 9.0  |
| H-5    | 3.56 | 3.46 | 3.41 | 5,6a   | 2.5  | 2.0  | 2.2  |
| H-6a   | 4.36 | 4.33 | 4.06 | 5,6b   | n.d. | n.d. | 4.3  |
| H-6b   | 4.03 | 4.06 | 3.92 | 6a,6b  | n.d. | 11.1 | 12.0 |
| H-1'   | 4.39 | 4.34 | 4.33 | 1',2'  | 7.8  | 7.7  | 7.8  |
| H-2'   | 5.09 | 5.06 | 5.06 | 2',3'  | 10.6 | 8.5  | 10.2 |
| H-3'   | 4.91 | 4.89 | 4.89 | 3',4'  | 3.4  | 3.4  | 2.5  |
| H-4'   | 5.32 | 5.31 | 5.31 | 4',5'  | 3.4  | 3.6  | 2.5  |
| H-5'   | 3.80 | 3.76 | 3.76 | 5',6'  | 6.7  | n.d. | 7.0  |
| H-6'a  | 4.07 | 4.06 | 4.10 | α,β    | 5.5  | 7.7  | 6.6  |
| H-6'b  | 4.07 | 4.06 | 4.10 | α,β'   | 4.5  | 7.7  |      |
| α-H    | 4.34 | 4.36 | 4.08 | β,β'   | 10.1 | n.d. |      |
| β-H    | 4.14 | 4.20 | 4.36 | β, CH$_3$ |   |      | 6.3  |
| β'-H   | 4.00 | 4.06 |      |        |      |      |      |
| OCH$_3$ | 3.69 |     | 3.66 |        |      |      |      |
| CH$_3$  |      |     | 1.14 |        |      |      |      |
| CHPh$_2$ |    | 6.84 |     |        |      |      |      |

Chemical shifts (p.p.m.)

| Number | 6 | 7 | 9 | 10 | 12 | 14 | 15 | 31 | 33 | 34[b] |
|---|---|---|---|---|---|---|---|---|---|---|
| H-1    | 4.57 | 4.62 | 4.70 | 4.57 | 4.64 | 4.64 | 5.00 | 4.58 | 4.57 | 4.76 |
| H-2    | 4.87 | 4.95 | 3.53 | 4.93 | 4.92 | 4.91 | 5.47 | 4.97 | 4.94 | 4.91 |
| H-3    | 5.13 | 5.19 | 5.10 | 5.13 | 5.16 | 5.13 | 5.82 | 5.19 | 5.17 | 5.05 |
| H-4    | 4.89 | 5.05 | 5.01 | 5.03 | 5.03 | 5.01 | 5.58 | 5.07 | 5.06 | 5.26 |
| H-5    | 4.05 | 3.63 | 3.59 | 3.54 | 3.49 | 3.39 | 3.82 | 3.69 | 3.61 | 3.89 |
| H-5'   | 3.31 |      |      |      |      |      |      |      |      |      |
| H-6    |      | 4.21 | 4.22 | 4.19 | 4.06 | 3.98 | 4.11 | 4.25 | 4.23 | 4.29 |
| H-6'   |      | 4.03 | 4.02 | 4.98 | 3.71 | 3.55 | 4.02 | 4.14 | 4.09 | 4.11 |
| α-H    | 4.36 | 4.35 | 4.43 | 4.43 | 4.12 | 4.20 | 4.21 | 3.62 | 3.67 | 3.86 |
| β-H    | 4.10 | 4.14 | 4.13 | 4.20 | 4.35 | 4.37 | 4.47 | 4.09 | 4.28 | 4.18 |
| β'-H   | 3.99 | 4.09 | 4.13 | 4.13 |      |      |      | 3.80 | 3.87 | 3.96 |
| OCH$_3$ | 3.70 | 3.69 |     |      | 3.68 |      |      | 3.73 |      |      |
| CH$_3$  |      |      |      |      | 1.15 | 1.08 | 0.97 |      |      |      |
| CHPh$_2$ |     | 6.90 | 6.86 |     | 6.85 | 6.80 |      | 6.87 |      |      |
| CH$_2$   |     | 4.72 |      |      |      |      |      |      |      |      |
| CH$_2$'  |     | 4.23 |      |      |      |      |      |      |      |      |

FIG 6a

Coupling constants (Hz)

| $J_{H,H}$ | 6 | 7 | 9 | 10 | 12 | 14 | 15 | 31 | 33 | 34[b] |
|---|---|---|---|---|---|---|---|---|---|---|
| 1,2 | 6.4 | 7.9 | 8.4 | 7.8 | 7.9 | 7.9 | 7.9 | 7.9 | 7.9 | 7.9 |
| 2,3 | 8.3 | 9.5 | 9.4 | 9.2 | 9.5 | 9.4 | 9.8 | 9.5 | 9.3 | 9.6 |
| 3,4 | 8.3 | 9.4 | 9.4 | 9.3 | 9.5 | 9.5 | 9.7 | 9.5 | 9.4 | 9.5 |
| 4,5 | 4.6 | 9.6 | 9.5 | 9.5 | 9.5 | 9.6 | 9.8 | 10.0 | 9.4 | 9.7 |
| 4,5' | 8.5 | | | | | | | | | |
| 5,5' | 12.2 | | | | | | | | | |
| 5,6 | | 4.3 | 4.3 | 4.5 | 4.0 | 3.7 | 3.0 | 4.8 | 4.4 | 4.3 |
| 5,6' | | 2.5 | 2.0 | 2.3 | 2.3 | 2.3 | 3.4 | 2.5 | 2.4 | 2.4 |
| 6,6' | | 12.2 | 12.1 | 12.3 | 12.3 | 12.3 | 12.2 | 12.3 | 12.5 | 12.8 |
| α,β | 6.5 | 6.0 | 5.9 | 6.1 | 7.0 | 7.4 | 7.7 | 5.0 | 4.3 | 2.9 |
| α,β' | 5.5 | 6.0 | 5.9 | 5.7 | 7.0 | | | 4.2 | 3.7 | 4.1 |
| β,β' | 10.9 | 6.4 | 5.6 | 10.2 | | | | 9.9 | 10.0 | 11.2 |
| β,CH$_3$ | | | | | 6.3 | 6.3 | 6.7 | | | |
| CH$_2$,CH$_2$' | | | 12.1 | | | | | | | |

[a]All nmr data is for solution in CDCl$_3$ unless otherwise indicated.
[b]Measured in CD$_3$OD$_3$.

FIG 6b

Table 2 $^{13}$C-NMR shifts of glycosides.[a]

| Number | 6 | 7 | 8 | 9 | 10 | 11 |
|---|---|---|---|---|---|---|
| C-1 | 100.81 | 101.05 | 100.20 | 100.95 | 100.85 | 100.29 |
| C-2 | 70.49 | 71.07* | 70.67* | 55.69 | 70.91 | 70.92* |
| C-3 | 71.27 | 72.79 | 71.30 | 71.37 | 72.70 | 71.57 |
| C-4 | 68.79 | 68.26 | 75.89 | 68.28 | 68.02 | 76.16 |
| C-5 | 61.75 | 71.70* | 72.23^ | 72.15 | 71.52 | 72.37 |
| C-6 | | 61.75 | 61.75 | 61.64 | 61.55 | 62.04 |
| C-1' | | | 100.79 | | | 101.07 |
| C-2' | | | 68.78 | | | 68.99 |
| C-3' | | | 70.32* | | | 70.63* |
| C-4' | | | 66.38 | | | 66.57 |
| C-5' | | | 72.64^ | | | 73.04 |
| C-6' | | | 60.58 | | | 60.78 |
| C=N | 172.10 | 172.14 | 171.81 | 172.30 | 172.19 | 172.23 |
| α-C | 65.29 | 65.29 | 64.96 | 65.62 | 65.56 | 65.54 |
| β-C | | 70.67 | 70.06 | 70.57 | 70.27 | 69.95 |
| CH$_3$ | | | | | | |
| OCH$_3$ | 52.14 | 52.14 | 51.94 | | | |
| HC(Ph)$_2$ | | | | 77.05 | 77.23 | 77.42 |
| CH$_2$CCl$_3$ | | | | 73.84 | | |
| NCH$_3$ | | | | | | |

| Number | 12 | 13 | 14 | 15 | 16 | 25b |
|---|---|---|---|---|---|---|
| C-1 | 99.38 | 98.51 | 100.06 | 100.89 | 99.79 | 99.61, 99.17 |
| C-2 | 70.59 | 70.61* | 71.25* | 71.48 | 70.77* | 70.44* |
| C-3 | 72.62 | 71.80 | 72.90 | 73.07 | 71.45 | 71.11 |
| C-4 | 67.83 | 75.74 | 68.00 | 69.57 | 75.94 | 75.91, 75.84 |
| C-5 | 71.41 | 72.17^ | 71.69* | 72.48* | 72.32 | 72.43 |
| C-6 | 61.24 | 61.57 | 61.35 | 62.55 | 61.81 | 61.64, 61.47 |
| C-1' | | 100.75 | | | 100.90 | 100.81 |
| C-2' | | 68.68 | | | 68.83 | 68.85 |
| C-3' | | 70.21* | | | 70.41* | 70.23* |
| C-4' | | 66.30 | | | 66.43 | 66.41 |
| C-5' | | 72.76^ | | | 72.88 | 72.43 |
| C-6' | | 60.50 | | | 60.64 | 60.63 |
| C=N | 171.54 | 171.33 | 171.70 | 171.82 | 171.51 | |

FIG 7a

| Number | 12 | 13 | 14 | 15 | 16 | 25b |
|---|---|---|---|---|---|---|
| $\alpha$-C | 71.41 | 70.67 | 71.84* | 72.25* | 66.14 | 58.49, 58.26 |
| $\beta$-C | 77.09 | 76.29 | 77.86 | 78.39 | 71.36 | 66.49 |
| $CH_3$ | 16.66 | 16.42 | 17.14 | 17.32 | | |
| $OCH_3$ | 51.77 | 51.74 | | | | 52.11 |
| $HC(Ph)_2$ | | | 77.25 | 77.27 | | |
| $CH_2CCl_3$ | | | | | | |
| $NCH_3$ | | | | | | 32.39, 32.04 |

| Number | 26b | 28 | 29b | 30 | 31 | 32 | 34c |
|---|---|---|---|---|---|---|---|
| C-1 | 100.76 | 97.20 | 101.04 | 97.38 | 100.74 | 100.96 | 101.90 |
| C-2 | 70.85* | 79.79 | 73.17 | 79.98 | 70.89 | 70.87* | 71.88 |
| C-3 | 71.23 | 81.82 | 76.64* | 82.04 | 72.45 | 71.44 | 73.20 |
| C-4 | 75.94 | 77.32 | 71.46 | 77.53 | 68.04 | 76.09 | 68.91 |
| C-5 | 72.44^ | 70.20 | 74.43* | 70.37 | 71.59 | 72.49 | 72.37 |
| C-6 | 61.70 | 68.61 | 62.57 | 68.72 | 61.60 | 61.82 | 62.17 |
| C-1' | 100.99 | | | | | 101.43 | |
| C-2' | 68.97 | | | | | 68.94 | |
| C-3' | 70.58* | | | | | 70.60* | |
| C-4' | 66.50 | | | | | 66.53 | |
| C-5' | 72.85^ | | | | | 72.88 | |
| C-6' | 60.73 | | | | | 60.73 | |
| C=N | | 172.21 | | 172.52 | | | |
| $\alpha$-C | 52.68 | 65.29 | 54.44 | 65.58 | 54.42 | 53.21 | 58.75 |
| $\beta$-C | 69.23 | 68.29 | 66.29 | 68.31 | 71.59 | 70.38 | 68.19 |
| $CH_3$ | | | | | | 14.06 | |
| $OCH_3$ | 52.68 | 52.15 | 53.93 | | 52.07 | | |
| $HC(Ph)_2$ | | | | | | | |
| $CH_2CCl_3$ | | | | | | | |
| $NCH_3$ | | | | | | | |

[a] Published nmr data was useful in making correct assignments,[51] measured in $CDC_3$ unless otherwise indicated.

[b] Measured in $CD_3OD$.

[c] For a solution in $CD_3OD_3$.

*,^ Assignments in the same column may be reversed.

FIG 7b

METHOD FOR MAKING AMINO ACID GLYCOSIDES AND GLYCOPEPTIDES

FIELD OF THE INVENTION

The field of the present invention is the creation of amino acid glycosides. Specifically, the field of the present invention is the creation of O-linked amino acid glycosides useful to create glycopeptides through the use of an imino bound intermediate.

BACKGROUND

Glycoproteins are proteins with covalently linked sugar residues. If these sugar residues are bound to a nitrogen-containing side chain of an amino acid, the sugar is termed "N-linked". If the sugar is bound to a hydroxyl side chain of an amino acid, the sugar is termed "O-linked".

In naturally occurring glycoproteins and in glycopeptide hormones, carbohydrate moieties play key roles in intercellular and intracellular transport of gene products (exit passport hypothesis),[2] as well as extending the biological half-life of the active peptides in vivo (proteolytic protection).[53] Additional roles supported by experimental evidence include the alteration of peptide backbone conformation (protein folding),[3] control of membrane permeability, and molecular recognition (the concept of carbohydrate "antennae").[4] These concepts have been summarized and amplified by Montreuil,[5] and have given birth to the field of "glycobiology".[6] The chemical synthesis of glycopeptides[7] provides an important tool for the study of glycopeptide hormones, glycoproteins and other complex carbohydrate structures found at the cell surface and in the glycocalyx.

Complex glycosides attached to exterior cell surfaces (N-linked glycoproteins, O-linked glycoproteins and glycolipids) are involved in the regulation of cell metabolism, host-pathogen interactions, tumor cell metastasis, cell-cell recognition, and cell adhesion. In order to fully define the roles complex carbohydrates play in these processes, and to thus understand "glycobiology" in its broadest sense, the synthesis of glycopeptides, glycolipids, and their structural analogues is required just as the chemical synthesis of DNA was required to understand molecular biology. O-linked glycopeptides are not as well understood as their N-linked counterparts.

Abnormalities in O-linked glycopeptides are implicated in numerous disease states. Abnormal post-translational modification of the tau protein has been implicated in the formation of neurofibrillary tangles of Alzheimer's disease.[8] The antigenic T-epitopes and $T_N$-epitopes of cell-surface glycopeptides have long been associated with cancer and used as tumor cell markers.[9] O-Glycosylated peptide fragments of these two proteins have been synthesized. Insulin-like growth factor (IGF-1),[10] oncofetal fibronectin Val-Thr-His-Pro-Gly-Tyr (SEQ ID NO: 1) fragment,[11] O-glycosylsomatostatin analogues,[12] O-glycosyltuftsin analogues,[13] O-glycosyl morphiceptin analogues,[14] glycophorin fragments,[15] and mucin fragments[16] have been synthesized for various biological studies.

The synthesis of O-linked glycopeptides is complicated by the acid-lability of glycosides in general and the base-sensitivity (retro-Michael reaction) of the O-serinyl and O-threonyl glycosides in particular.[17] Although Boc has been used for N-terminus protection,[12a] use of the Fmoc-based peptide coupling strategies (solution[9b,11] or solid-phase[10] methodology) or Cbz-based strategies[13,14,15] voids acidic conditions for deprotection of the N-termini and appears to be superior. Glycosylation of intact, resin-bound peptides has been attempted,[8] but does not appear to be a generally applicable approach. Acid-labile resin linkers[14,16,18] permit cleavage of the O-linked glycopeptides from the solid-phase support without exposure of the glycoside-bearing residues to strong acids.

The stereoselective synthesis of protected amino acid glycosides remains challenging. Glycosylation of N-acylated β-amino alcohols such as Fmoc-protected or Cbz-protected serine and threonine derivatives, as well as the structurally related ceramides and protected sphingosines[20] is not efficient. Problems encountered by the pioneers[17,21] in this area include low yields and poor α/β selectivity.

Szabo, et al.[1] created Schiff base intermediates to facilitate O-linked glycosylation. However, the Szabo, et al. products were protected with methyl groups at the carboxyl terminus of the aminoacid. Methyl groups are not removable under standard peptide synthesis conditions. Thus, these glycosides could not be used to create glycopeptides.

What is needed in the art is an improved method to create amino acid glycosides that are useful to make glycopeptides.

SUMMARY OF THE INVENTION

The present invention is a compound of the formula:

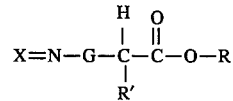

wherein X is an imino-bound moiety selected from the group consisting of alkyl, aryl, imidate ester, imino ester, amidine, azide, isocyanate, and dithiocarbonate groups. R' is a group containing a hydroxyl moiety or a protected hydroxyl moiety or an O-linked sugar. R is not a methyl group and is a group capable of removal under conditions compatible with glycopeptide synthesis and existance. G is a carbon chain of 0–10 carbons.

In a particularly preferred form of the invention, R is either an benzylic or allyl group, X is $CPh_2$ and R' is either $CH_2OH$ or $CH(OH)CH_3$.

The present invention is also a compound of the formula:

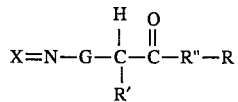

wherein X is an imino-bound moiety selected from the group consisting of alkyl, aryl, imidate ester, imino ester, amidine, azide, isocyanate, and dithiocarbonate groups. R' is a group containing a hydroxyl moiety, a protected hydroxyl moiety, or an O-linked sugar. R" is an amino acid chain. R is not a methyl group and is a group capable of removal under conditions compatible with glycopeptide synthesis. G is a carbon chain of 0–10 carbons. Preferably, R" is an amino acid chain of less than 13 residues. Most preferably, R" is a chain of less than 3 residues.

The present invention is also a method of creating an amino acid glycoside comprising the steps of creating the compound described above, wherein R' is a protected hydroxyl group or a hydroxyl group, and exposing this compound to a sugar under conditions wherein a hydroxyl residue in the R' group is substituted with the sugar residue.

The present invention is also a method of creating a glycosylated peptide comprising the steps of creating an amino acid glycoside described above and incorporating the glycoside into a peptide chain.

It is an object of the present invention to create an intermediate compound useful in the formation of glycosides and glycopeptides.

It is another object of the present invention to provide a method by which glycopeptides may be synthesized.

It is a feature of the present invention that O-linked amino acid glycosides may be provided which are suitable substrates in standard peptide synthesis reactions.

It is another feature of the present invention that the group protecting the carboxyl terminus of the amino acid glycoside or amino acid chain glycoside is protected by a group that is capable of removal under conditions compatible with glycopeptide synthesis.

Other objects, advantages, and features of the present invention will become apparent after examination of the specification, claims, and drawings.

DESCRIPTION OF THE DRAWINGS

FIG. 3 is a chart describing different imino intermediate acceptor molecules, different sugar donor molecules, and the different products produced by each reaction.

FIGS. 6a and 6b are two parts of a table describing $^1$H-nmr chemical shift assignments and coupling constants for the β-glycoside products.

FIGS. 7a and 7b are two parts of a table listing $^{13}$C-nmr chemical shift assignments.

DESCRIPTION OF THE INVENTION

A. In General

Figure 1:
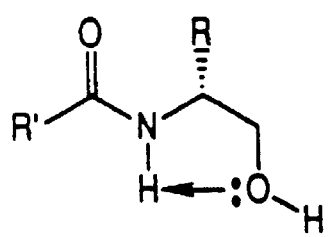
FIG. 1 is a diagram describing favorable and unfavorable hydrogen bonding patterns.
Figure 1:
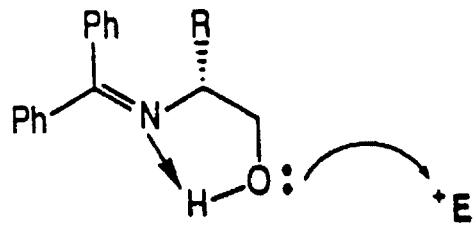

Previous attempts to create an O-linked amino acid glycoside were not successful enough to create glycosides that could readily be incorporated into peptides. Previous workers have encountered low yields ant poor α/β selectivity. We attribute these problems to the decreased nucleophilicity of the glycosyl acceptor due to an unfavorable hydrogen bonding pattern. Conversely, we reasoned that if a favorable hydrogen bonding pattern were generated, that the nucleophilicity of the neighboring hydroxyl would be increased. FIG. 1 describes these favorable and unfavorable hydrogen bonding patterns. Preliminary experiments[1] have confirmed this hypothesis.[20,22]

The present invention involves the use of this concept in the development of methods for the synthesis of either α- or β-O-linked glycopeptides and its application to the synthesis of specific glycopeptides of interest, such as the O-glycosyl analogue of DPDPE,[23] a potent δ-opioid receptor selective agonist.[24] In the present invention an intramolecular hydrogen bond (C=N:→H—O:) is used to enhance the nucleophilicity of amino acid hydroxyl side chains, We demonstrate in the Examples that imino-bound intermediates, in particular Schiff bases of α-amino esters (O'Donnell's Schiff bases[25]), are useful intermediates for the synthesis of O-linked glycopeptides when the group protecting the carboxyl terminus of the amino acid or amino acid chain is not a methyl group but is, instead, a group capable of being removed from the terminus under conditions suitable for peptide synthesis.

In the Examples below, we demonstrate efficient β- and α-selective glycosylations of serine and threonine residues using the classical Koenigs-Knorr reaction and Lemieux's in situ anomerization methodology with Schiff base intermediates. Purification of the glycosyl Schiff bases is straightforward. The Examples indicate that deprotection of these Schiff base glycosides has been accomplished using mildly acidic conditions or hydrogenolysis. We then demonstrated solution phase and solid phase peptide syntheses using the glycosyl Schiff bases as starting materials.

B. Creation of α and β O-linked Glycosides Through an Imino-bound Intermediate

The method of the present invention begins with the creation of glycosides from amino acids with hydroxyl side chains, such as serine and threonine. Other amino acids that may contain hydroxyl side chains, such as artificially created amino acids or rarely occurring amino acids, would also be suitable for the present invention. Alternatively, the starting material may be an amino acid chain, such as the ser-gly chain described in FIG. 2 and discussed in the Examples below. Preferably this chain is of less than 13 residues. Most preferably, the chain is of less than 3 residues.

The amino acid is first modified so that the amino moiety of the amino acid is part of an imino bound intermediate. By "imino bound" we mean any double-bonded atom, or group of atoms, which is ultimately converted to an amine or peptide amide. X may be any imino-bonded moiety such as all imine (alkyl$_2$ C=), Schiff base (aryl$_2$ C=)or(aryl (H)C=), imidate or imino ester (alkyl-O(H)C=) or (aryl-O(H)C=), amidine (alkyl$_2$ N(H) C=) or (aryl$_2$ N(H) C=), azide (N=N=), isocyanate (O=C=), and dithiocarbonate ((alkyl-S)$_2$ C=). Preferably, X is a CPh$_2$ group. A particularly useful class of imino-bound intermediates is a Schiff base.

Figure 2:
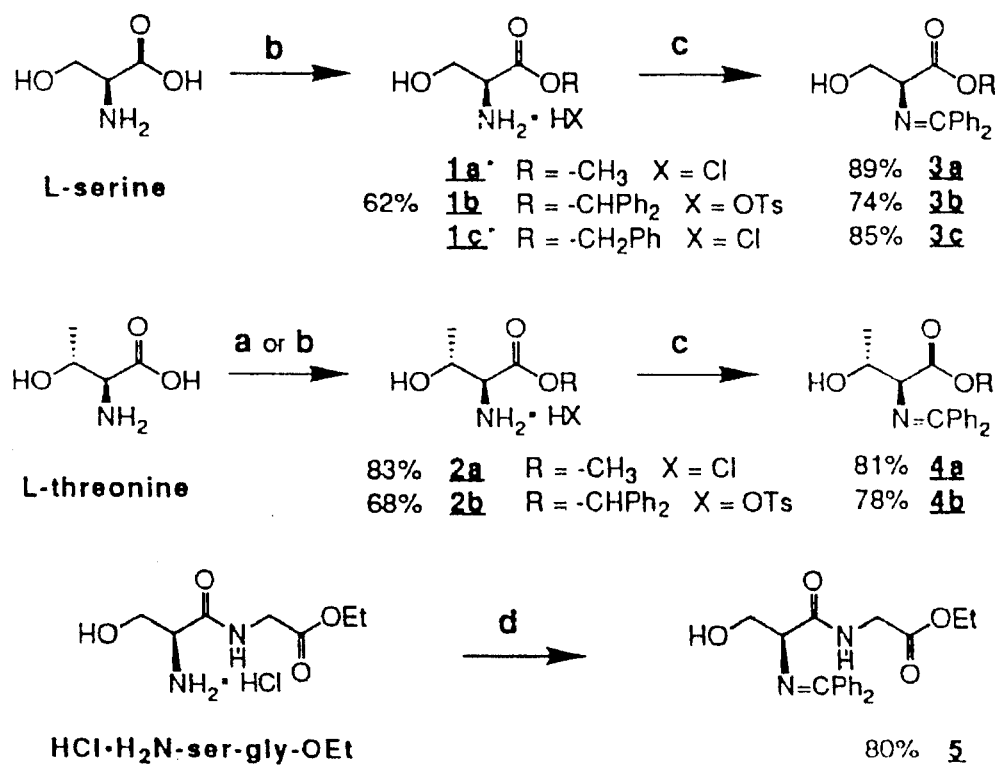
FIG. 2 describes three chemical reactions resulting in imino bound intermediates.

FIG. 2 (discussed in the Examples) demonstrates the creation of exemplary Schiff bases, 3a, 3b, 3c, 4a, 4b and 5. The amino acid is obtained and modified to a compound of the general formula R'—C(NH$_2$.HX)—COOR where X is preferably Cl or OTs and R is preferably either CHPh$_2$ or CH$_2$Ph. R' is a hydroxyl-containing group. For instance, if the amino acid is serine, R' is C—OH. However, R' could be a group containing a protected hydroxyl group, such as an ether or ester moiety.

The R group protects the carboxyl group. The Examples contain compounds in which the protecting R-group is a methyl or an ethyl group. These examples are included only to demonstrate the efficacy of creation of the amino acid glycosides. In actual practice these methyl-protected and ethyl-protected compounds have limited efficacy because of the difficulty in creating a peptide from these compounds.

In the method of the present invention, the R-group is not a methyl group. However, other R-groups besides CHPh$_2$ and $CH_2Ph$ are suitable. For example, allyl, silyl, and phenacyl groups are suitable. The group can also be aryl or halogen. In general, benzylic and allyl groups are preferred as protecting R groups because of the ease of removing these groups during peptide formation. Particularly suitable aromatic or allyl groups are P-nitrophenyl ($C_6H_5$—$NO_2$), halogenated phenyl, and substituted allyl groups.

In the Examples below, serine and threonine are treated with TsOH and $Ph_2C$=$N_2$/DMF at 60° C. to produce the desired intermediate. Additionally, threonine may be treated with $MeOH/SOCl_2$ at 0° C. However, there are other methods known to produce these intermediates.

These intermediate compounds can be commercially available. For instance, compound 1C is available from Aldrich Chemical.

This intermediate compound is preferably treated with $Ph_2C$=NH and either $CH_2Cl_2$ or $CH_3CN$, preferably at RT, to create the desired imine intermediate. Suitable reaction conditions are described in the Examples below.

C. Addition of Sugar Residue

After the creation of the imine intermediate, the hydroxyl side chain has become more electrophillic. Therefore, selective glycosylation may occur. Both α- and β-glycosides can be created. Preferably, the Hanessian modification[30] or Helferich's modification of the Koenigs-Knorr reaction[29] are used to create β-glycosides. The Examples below describe suitable reaction conditions. Any standard glycosylation method should work because the present invention enhances the reactivity of the alcohol, the glycosylation acceptor.

To create α-glycosides, preferably the anomerization method of Lemieux[36] is used. The Examples below describe suitable reaction conditions.

The method of the present invention is also amenable to the synthesis of amino acid glycosides via block-type transfers of polysaccharide donors due to the mild conditions required for glycosylation of the Schiff bases. Groups of sugars, rather than single sugars, may be added by using block-transfer methods, such as thioglycosides of polysaccharides.

D. Suitable Sugars

Suitable sugars for use in the present invention include both pyranoses and furanoses. The sugars should first be protected and modified by standard methods, such as those described by Paulson,[7e] Kunz,[7b] or Schmidt.[7c] Sugars useful in glycosylation reactions such as the Hanessian modification and Koenigs-Knorr reaction are suitable for the present invention. Many of these sugars are available commercially.

E. Creation Of Glycosylated Peptides

The Examples below demonstrate both solid phase and liquid phase creation of peptides from the amino acid glycosides. Both methods are suitable for creation of glycopeptides. To create a peptide, methods known to those in the art, such as those disclosed in the Examples below, are suitable. Specific examples of glycopeptides that may be created using the method of the present invention are DPDPE (as demonstrated in the Examples below) and other neurologically active peptides. However, the present invention is meant to encompass the creation of any biologically active or inactive glycopeptide.

The amino acid glycoside must have a carboxyl group protected by a group removable under conditions suitable for glycoprotein synthesis. By "conditions compatible with glycopeptide synthesis" we mean in general conditions which are neither too acidic nor basic for the existence of glycopeptides. Specifically, the Examples give descriptions of suitable solid-phase and solution-phase peptide synthesis conditions. Both the polysaccharide linkages and the peptide linkages must survive conditions for deprotection and coupling.

EXAMPLES

A. General Methods

Resins and Fmoc-amino acids were purchased from Bachem California, Torrance, Calif. All air and moisture sensitive reactions were performed under an argon atmosphere in flame-dried reaction flasks. THF was dried and de-oxygenated over $Ph_2C$=O/Na°-K°. $CH_2Cl_2$ and $CH_3CN$ were dried over $P_2O_5$ and all solvents were freshly distilled under an argon atmosphere prior to use. For flash chromatography,[31] 400–230 mesh silica gel 60 (E. Merck No. 9385) was employed. All compounds described were >95% pure by $^1H$- and $^{13}C$-NMR, and purity was confirmed by elemental analysis in many cases. The $^1H$- and $^{13}C$-NMR spectra were obtained on a Bruker WM-250 spectrometer at 250 and 62.9 MHz respectively. COSY spectra were obtained on a Bruker WM-500 spectrometer at 500 MHz. Chemical shifts are reported in δ vs $Me_4Si$ in $^1H$ spectra and vs. $CDCl_3$ in $^{13}C$ spectra. Infrared spectra were obtained on a Perkin Elmer 1600 Series FT IR. All melting points were measured on a Hoover capillary melting point apparatus and are uncorrected. Optical rotations were measured on a Randolph Research, AutoPol III polarimeter using the Na-D line. Elemental analyses were performed by Desert Analytics, Tucson, Ariz. 85719. Nominal and exact mass spectra were obtained on a JEOL JMS-01SG-2 mass spectrometer.

Methods of creating Specific compounds used in the examples are described below:

Diphenylmethyl-N-(diphenylmethylene)-L-serinate, (3b)

The procedure used was that of O'Donnell.[25] Diphenylmethyl-L-serinate salt, (1b) (24.39 g, 55 mmol), $Ph_2C$=NH (9.06 g, 50 mmol), and $CH_2Cl_2$ (80 mL) were stirred at RT for 24 h with the exclusion of moisture ($CaCl_2$ tube). The reaction mixture was diluted with $CH_2Cl_2$ (100 mL), filtered, and washed with 1% $NaHCO_3/H_2O$ (3×30 mL) to remove the precipitated $NH_4Cl$. The organic layer was dried ($MgSO_4$) and evaporated. The resulting mass was recrystallized from $Et_2O$/hexane to give 16.11 g 3b (74%); m.p. 137°–9° C.; $[α]^{20}_D$=−112° (c=1.0, $CHCl_3$). $R_f$ 0.46 (hexane/EtOAc 8:2). Anal Calcd. for $C_{29}H_{25}O_3N$: C, 79.98; H, 5.79; N, 3.22. Found: C, 79.87; H, 5.84; N, 3.10.

Benzyl-N-(diphenylmethylene)-L-serinate, (3c)

Reaction as in 3b. Recrystallization (cyclohexane) provided pure 3c in 85% yield m.p. 78° C. $[α]^{20}_D$=−120.4° (c=0.9, $CHCl_3$). $R_f$ 0.47 (hexane/EtOAc 81:19). Anal. Calcd. for $C_{23}H_{21}O_3N$: C, 76.86; H, 5.89; N, 3.90. Found: C, 76.59; H, 5.98; N, 3.73.

Methyl-N-(diphenyl methylene)-L-threoninate, (4a)

Reaction as in 3b. Recrystallization ($Et_2O$/hexane) provided pure 4a in 81% yield. m.p. 82.5°–84.5° C. $[α]^{20}_D$=−146° (c=1.1, $CHCl_3$). $R_f$ 0.54 (hexane/EtOAc 7:3). Anal. Calcd. for $C_{18}H_{19}O_3N$: C, 72.71; H, 6.44; N, 4.71. Found: C, 72.80; H, 6.40; N, 4.59.

Diphenylmethyl-N-(diphenylmethylene)-L-threoninate, (4b)

Reaction as in 3b. Recrystallization (Et$_2$O/hexane) provided 4b in 78% yield. m.p. 107°–9° C. $[\alpha]^{20}{}_D$=−111° (c=1.0, CHCl$_3$); R$_f$ 0.24 (hexane/EtOAc 9:1); Anal. Calcd. for C$_{30}$H$_{27}$O$_3$N: C, 80.15; H, 6.05; N, 3.12. Found: C, 80.31; H, 5.97; N, 2.99.

Ethyl-N-[N-(diphenylmethylene)-L-serinyl]glycinate, (5)

Reaction as in 3b. Recrystallization (Et$_2$O/hexane) provided 5 in 80% yield m.p. 103°–5° C. $[\alpha]^{20}{}_D$=+59.5° (c=0.21, CHCl$_3$). R$_f$ 0.18 (hexane/EtOAc 55:45). Anal. Calcd. for C$_{20}$H$_{22}$O$_4$N$_2$: C, 67.78; H, 6.26; N, 7.90. Found: C, 67.54; H, 6.22; N, 7.71.

Methyl-N-(diphenylmethylene)-L-serinate-O-(2,3,4-tri-O-acetyl)-β-D-xylo-pyranoside, (6)

Methyl-N-(diphenylmethylene)-L-serinate,[27] 3a (447 mg, 1.58 mmol), acetobromoxylose,[48] 17(535 mg, 1.2 eq), powdered, oven-dried 4 Å molecular sieves (1.5 g), and CH$_2$Cl$_2$ (10 mL) were stirred at 0° under argon for 10 min. Silver triflate (492 mg, 1.2 eq) was added in portions over 10 min, and stirring was continued for 14 hrs. The reaction was quenched with Et$_3$N (0.5 mL), diluted with CH$_2$Cl$_2$ (30 mL), filtered through celite and the organic layer was washed with saturated NaHCO$_3$ (3×15 mL), H$_2$O (3×15 mL), and dried (MgSO$_4$). Rotary evaporation and flash chromatorgraphy[31] on 50 g of SiO$_2$ with hexanes/EtOAc 6:4 (R$_f$ 0.49) provided 804 mg pure 6 as a syrup (94%). For $^1$H and $^{13}$C-nmr data, see FIGS. 6a, 6b, 7a and 7b. $[\alpha]^{20}{}_D$=−78° (c=0.46, CHCl$_3$). Anal. Calcd. for C$_{28}$H$_{31}$O$_{10}$N: C, 62.09; H, 5.77; N, 2.58 Found: C, 62.28; H, 5.81; N, 2.51.

Methyl-N-(diphenylmethylene)-L-serinate-O-(2,3,4,6-tetra-O-acetyl)-β-D-glucopyranoside, (7)

Methyl-N-(diphenylmethylene)-L-serinate,[27] 3a (1.11 g, 3.9 mmol), acetobromoglucose, 18 (1.93 g, 1.2 eq), powdered, oven-dried 4 Å molecular sieves (2.0 g) and CH$_2$Cl$_2$ (20 mL) were stirred at 0° under argon for 10 min. Silver triflate (1.2 g, 1.2 eq) was added in portions over 20 min, and stirring was continued for 14 hrs. The reaction was quenched with Et$_3$N (0.7 mL), diluted with CH$_2$Cl$_2$ (60 mL), filtered through celite and the organic layer was washed with saturated NaHCO$_3$ (3×15 mL), H$_2$O (3×15 mL), and dried (MgSO$_4$). Rotary evaporation and flash chromatorgraphy[31] on 100 g of SiO$_2$ with hexanes/EtOAc 55:45 (R$_f$ 0.61) provided 2.01 g pure 7 as a syrup (83.6%). For $^1$H and $^{13}$C-nmr data, see FIGS. 6a, 6b, 7a and 7b. $[\alpha]^{20}{}_D$=−48.0° (c=0.82, CHCl$_3$). Anal. Calcd. for C$_{31}$H$_{35}$O$_{12}$N: C, 60.67; H, 5.74; N, 2.28. Found: C, 60.49; H, 5.82; N, 2.19.

Methyl-N-(diphenylmethylene)-L-serinate-O-(2,3,6,2',3',4',6'-hepta-O-acetyl)-β-D-lactoside, (8)

Method A (Modified Koenigs-Knorr[30] Reaction): Reaction as in (3a→7) above, using 3a. (849mg, 3.0 mmol), and acetobromolactose,[49] 20 (2.52 g, 1.2 eq), to provide 2.02 g 8 as a foam (88%) after chromatography[31] (R$_f$ 0.8 CH$_2$Cl$_2$/acetone 87:13). For $^1$H and $^{13}$C-nmr data, see FIGS. 6a, 6b, 7a and 7b. $[\alpha]^{20}{}_D$=−29.7° (c=1.26, CHCl$_3$). Anal. Calcd. for C$_{43}$H$_{51}$O$_{20}$N: C, 57.26; H, 5.70; N, 1.55. Found: C, 57.41; H, 5.58; N, 1.57. Method B (Kochetkov[52] Method): Orthoester 22 (626 mg, 1.0 eq.), Schiff base 3a (59 mg, 0.30 eq.), powdered, oven-dried 4 Å molecular sieves (1.5 g) and CH$_2$Cl$_2$ (10 mL) were stirred at RT under argon for 10 minutes. Silver triflate (178 mg, 1.0 eq) was added into this mixture, and stirring was continued overnight. Work-up as in (3a→7) above, provided 395 mg 8 (63%).

Diphenylmethyl-N-(diphenylmethylene)-L-serinate-O-[3,4,6-tri-O-acetyl-2-deoxy-2-(2,2,2-trichloroethoxycarbonylamino)]-β-D-glucopyranoside, (9)

Reaction as in (3a→7) above, using 3b (449.5 mg, 1.00 mmol) and bromide 21[50] (815.4 mg, 1.5 eq), provided 747 mg 9 after chromatography[31] (R$_f$ 0.43 hexene/EtOAc 6:4) as a foam (81%). For $^1$H and $^{13}$C-nmr data, see FIGS. 6a, 6b, 7a and 7b. $[\alpha]^{20}{}_D$=−7.9° (c= 0.9, CHCl$_3$). Anal. Calcd. for C$_{44}$H$_{43}$O$_{12}$N$_2$Cl$_3$: C, 58.84; H, 4.83; N, 3.12. Found: C, 58.49; H, 4.97; N, 3.01.

Diphenylmethyl-N-(diphenylmethylene)-L-serinate-O-(2,3,4,6-tetra-O-acetyl)-O-β-D-glucopyranoside, (10)

Reaction as in (3a→7) above, using 3b, to provide 10 in 77% yield as a syrup after chromatography[31] (R$_f$ 0.5 hexanes/EtOAc 6:4) For $^1$H and $^{13}$C-nmr data, see FIGS. 6a, 6b, 7a and 7b. $[\alpha]^{20}{}_D$ =−24° (c=0.6, CHCl$_3$). Anal. Calcd. for C$_{43}$H$_{43}$O$_{12}$N: C, 67.43; H, 5.65; N, 1.82. Found: C, 67.27; H, 5.82; N, 1.69.

Diphenylmethyl-N-(diphenylmethylene)-L-serinate,-3,6,2',3',4',6'-hepta-O-acetyl)-β-D-lactoside, (11)

Reaction as in (3a→7) above, except 1.0 eq. acceptor 3b, 1.6 eq. donor 20, and 1.6 eq. AgSO$_3$CF$_3$ were used to provide 11 as a foam in 79% yield after chromatography[31] (R$_f$ 0.53 hexanes/EtOAc 45:55). For $^1$H and $^{13}$C-nmr data, see FIGS. 6a, 6b, 7a and 7b. $[\alpha]^{20}{}_D$=−19.5° (c=0.65, CHCl$_3$). Anal. Calcd. for C$_{55}$H$_{59}$O$_{20}$N: C, 62.67; H, 5.64; N, 1.33. Found: C, 62.74; H, 5.58; N, 1.21.

Methyl-N-(diphenylmethylene)-L-threoninate-O-(2,3,4,6-tetra-O-acetyl)-β-D-glucopyranoside, (12) and 1,2-O-[methyl-N-(diphenylmethylene)-L-threonate-O-ethylidene]-(3,4,6-tri-O-acetyl)-α-D-glucopyranose, (12a)

Reaction as in (3a→7) above, using Schiff base 4a (892 mg, 3.00 mmol) and acetobromoglucose 18 (1.60 g, 1.3 eq), to provide 1.20 g 12 as a syrup (64%) after chromatography[31] (R$_f$ 0.34 hexanes/EtOAc 65:35). For $^1$H and $^{13}$C-nmr data, see FIG. 6 and 7. $[\alpha]^{20}{}_D$=−72.8° (c=0.9, CHCl$_3$). Anal. Calcd. for C$_{32}$H$_{37}$O$_{12}$N: C, 61.23; H, 5.94; N, 2.31. Found: C, 61.40; H, 6.02; N, 2.21. Orthoester 12a (R$_f$ 0.54), also was isolated (330 mg, 17%). m.p. 115°–116° C. (recrystallized from hexanes/EtOAc). $[\alpha]^{20}{}_D$=−38° (c=0.34, CHCl$_3$). Characteristic nmr-data: $^1$H-nmr (CDCl$_3$) δ7.66-7.15 (m,10H, aromatic H), 5.60(d, 1H, H-1, J$_{1,2}$=4.2 Hz), 3.68 (s, 3H, OCH$_3$), 2.09, 2.08, 2.02 (3s, 9H, 3 O=C—CH$_3$), 1.69 (s, 3H, orthoester CH$_3$), 1.19 (d, 3H, CH$_3$). $^{13}$C-nmr (CDCl$_3$)δ121.37 (orthoester 4° C.), 96.64 (C1), 63.03 (C6), 51.85 (OCH$_3$), 21.62 (orthoester CH$_3$), 18.50 (CH$_3$). Anal. Calcd. for C$_{32}$H$_{37}$O$_{12}$N: C, 61.23; H, 5.94; N, 2.31. Found: C, 61.22; H, 5.89; N, 2.17.

Methyl-N-(diphenylmethylene)-L-threoninate-O-(2,3,6,2',3',4',6'-hepta-O-acetyl)-β-D-lactoside, (13).

Reaction as in (3a→7) above, using 4a (892 mg, 3.00 mmol) and 20 (2.72 g, 1.3 eq), to provide 2.23 g 13 as a foam (81%) after chromatography[31] ($R_f$ 0.40 hexanes/EtOAc 45:55). For $^1$H and $^{13}$C-nmr data, see FIGS. 6a, 6b, 7a and 7b. $[\alpha]^{20}{}_D=-37°$ (c=0.96, CHCl$_3$). Anal. Calcd. for C$_{44}$H$_{53}$O$_{20}$N: C, 57.69; H, 5.83; N, 1.52. Found: C, 57.82; H, 5.89; N, 1.38.

Diphenylmethyl-N-(diphenylmethylene)-L-threoninate-O-(2,3,4,6-tetra-O-acetyl)-β-D-glucopyranoside, (14).

Reaction as in (3a→7) above, to give 14 from 4b and 18 in 45% yield as a foam after chromatography[31] ($R_f$ 0.52 hexanes/EtOAc 6:4). For $^1$H and $^{13}$C-nmr data, see FIGS. 6a, 6b, 7a and 7b. $[\alpha]^{20}{}_D=-49.5°$ (c=2.3, CHCl$_3$). Anal. Calcd. for C$_{44}$H$_{45}$O$_{12}$N: C, 67.77; H, 5.82; N, 1.80. Found: C, 67.91; H, 5.66; N, 1.67.

Diphenylmethyl-N-(diphenylmethylene)-L-threoninate-O-(2,3,4,6-tetra-O-benzoyl)-β-D-glucopyranoside, (15)

Reaction as in (3a→7) above, to give 15 from 4b and 19 in 63% yield as a foam after chromatography[31] ($R_f$ 0.47 hexanes-EtOAc 7:3) For $^1$H and $^{13}$C-nmr data, see FIGS. 6a, 6b, 7a and 7b. $[\alpha]^{20}{}_D=-2.0°$ (c=1.2, CHCl$_3$). Anal. Calcd. for C$_{64}$H$_{53}$O$_{12}$N: C, 74.77; H, 5.20; N, 1.36. Found: C, 74.62; H, 5.34; N, 1.21.

N-(diphenylmethylene)-O-(2,3,6,2',3',4',6'-hepta-O-acetyl-β-D-lactosyl)-(1→3)-L-serinyl-L-glycine ethylester (16)

Coupling as described for 7 to give 16 in 86% yield as an amorphous solid after chromatography[31] ($R_f$ 0.6 hexanes/EtOAc 25:75). $[\alpha]^{20}{}_D=-6.2°$ (c=0.64, CHCl$_3$) Characteristic $^1$H-nmr data: $^1$H-nmr (CDCl$_3$)δ7.70-7.14 (m, 10H, aromatic H), 4.46 (d, 1H, H-1, $J_{1,2}$=7.6 Hz), 4.39 (d, 1H, H-1', $J_{1',2}$=7.8 Hz), 2.14-1.94 (7s, 21H, 7 O=CCH$_3$), 1.28 (t, 3H, CH$_2$CH$_3$). For $^{13}$C-nmr data, see FIGS. 7a and 7b. Anal Calcd. for C$_{46}$H$_{56}$O$_{21}$N$_2$: C, 56.78; H, 5.80; N, 2.87. Found: C, 56.57; H, 5.68; N, 2.78.

1,2-O-[Methyl-N-(diphenylmethylene)-L-serinate-O-ethylidene]-3,6-di-O-acetyl-(2,3,4,6-tetra-O-acetyl-β-D-galactopyranosyl)-α-D-glucopyranose, (22)

A mixture of acetobromolactose 20 (435 mg, 0.62 mmol), Schiff base 3a (180 mg, 0.636 mmol), and NaHCO$_3$ (185 mg, 2.2 mmol) were stirred in THF (12 mL) at 0° C. for 10 min. Then a solution of AgOT$_f$l (183 mg in 8 mL THF) was added dropwise. After 10 min the reaction mixture was poured into ice water and extracted with CH$_2$Cl$_2$. The organic layer was separated and washed with cold H$_2$O, sat. NaHCO$_3$, dried (MgSO$_4$), and evaporated. The residue was chromatographed[31] ($R_f$ 0.25 hexanes/EtOAc 55:45) and recrystallized (Et$_2$O/Pentane) to give 250 mg 22 (45%). m.p. 93°-95° C. $[\alpha]^{20}{}_D=-35°$ (c, 0.21 CHCl$_3$) Characteristic nmr-data: $^1$H-nmr (CDCl$_3$) δ7.65-7.15 (m, 10H, aromatic H), 5.58 (dr 1H, H-1, $J_{1,2}$=4.6 Hz), 4.51 (d, 1H, H-1', $J_{1',2}$=7.9 Hz), 3.73 (s, 3H, O[***]), 2.18-1.96 (6s, 18H, 6 O=CCH$_3$), 1.68 (s, 3H, orthoester CH$_3$). $^{13}$C-nmr (C$_6$D$_6$) δ 121:77 (orthoester 4° C.), 103.14 (C1'), 97.22 (C1), 78.47 (C4), 64.16 (C6), 60.98 (C6'), 51.61 (OCH$_3$). Anal. Calcd. for C$_{43}$H$_{51}$O$_{20}$N: C, 57.26; H, 5.70; N, 1.55. Found: C, 57.29; H, 5.79; N, 1.48.

1,2-O-[Methyl-N-(diphenylmethylene)-L-threoninate-O-ethylidene]-3,6-di-O-acetyl-(2,3,4,6-tetra-O-acetyl-β-D-galactopyranosyl)-α-D-glucopyranose, (23)

Reaction as in (3a→22) above, with Schiff base 4a and acetobromolactose 20 to give 23 in 55% yield after chromatography[31] ($R_f$ 35 hexanes/EtOAc 1:1), and recrystallization (hexanes/EtOAc) m.p. 158°-160° C. $[\alpha]^{20}{}_D=-29°$ (c=0.5, CHCl$_3$). Characteristic nmr-data: $^1$H-nmr (CDCl$_3$) δ 7.66-7.15 (m, 10H, aromatic H), 5.53 (d, 1H, H-1, $J_{1,2}$=4.9 Hz), 4.58 (d, 1H, H-1', $J_{1',2}$=8.0 Hz), 3.68 (s, 3H, OCH$_3$), 2.17-1.97 (6s, 18H, 6 O=CCH$_3$), 1.69 (s, 3H, orthoester CH$_3$), 1.20 (d, 3H, CH$_3$). $^{13}$C-nmr (CDCl$_3$) δ121.40 (orthoester 4° C.), 101.92 (C1'), 96.49 (C1), 77.37 (C4), 63.21 (C6), 60.74 (C6'), 51.72 (OCH$_3$), 21.30 (orthoester CH$_3$), 18.42 (CH$_3$). Anal. Calcd. for C$_{44}$H$_{53}$O$_{20}$N: C, 57.69; H, 5.83; N, 1.52. Found: C, 57.77; H, 5.72; N, 1.41.

1,2-O-[Methyl-N-(diphenylmethylene)-L-serinate-O-ethylidene]-3,4,6-tri-O-acetyl-α-D-glucopyranose, (24)

Reaction as in (3a→22) above, with Schiff base 3a and acetobromoglucose 18 to give 24 in 52% yield after chromatography[31] ($R_f$ 0.2 hexanes/EtOAc 7:3) and recrystallization (Et$_2$O/pentane). m.p 49°-51° C. $[\alpha]^{20}{}_D=-35°$ (c=0.4, CHCl$_3$). Characteristic nmr-data: $^1$H-nmr (CDCl$_3$)δ 7.64-7.18 (m, 10H, aromatic H), 5.61 (d, 1H, H-1, $J_{1,2}$=5.2 Hz), 3.71 (s, 3H, OCH$_3$), 2.09, 2.08, 2.04 (3s, 9H, 3 O=CCH$_3$), 1.67 (s,3H, orthoester CH$_3$). $^{13}$C-nmr (CDCl$_3$) δ 120.93 (orthoester 4° C.), 96.61 (C1), 64.29 (β-C), 62.94 (C6), 52.12 (OCH$_3$). Anal. Calcd. for C$_{31}$H$_{35}$O$_{12}$N: C, 60.67; H, 5.74; N, 2.28. Found: C, 60.71; H, 5.89; N, 2.20.

Methyl-N-(benzyloxycarbonyl)-N-(methyl)-L-serinate, (25a).

N-Methyl-L-serine (Schweizerhall Inc.) (800 mg) was suspended in dry MeOH (8 mL) and cooled to −10° C. To this solution was dropped SOCl$_2$ (0.64 mL) with vigorous stirring. After refluxing for 4 hrs, the product was triturated in dry Et$_2$O and filtered. The resulting precipitate was suspended in dry CH$_2$Cl$_2$ (12 mL), and cooled to 0° C. Et$_3$N (2.8 mL) and PhCH$_2$ COCl (0.9 mL) were dropped simultaneously. The stirring was continued for 14 hrs at RT, and the reaction mixture was diluted CH$_2$Cl$_2$ (30 mL), washed with 0.5N HCl (3×10 mL), H$_2$O, dried (MgSO$_4$), and filtered. Chromatography[31] ($R_f$ 0.5 hexanes/EtOAc 4:6) provided 1.31 g 25a as a syrup (73.1%). Characteristic nmr-data: $^1$H-nmr (CDCl$_3$) δ 7.36-7.26 (m, 5H, aromatic H), 5.15, 5.11 (s, 2H, CH$_2$Ph), 4.61, 4.49 (t, 1H, α-H), 4.07, 3.95 (m, 2H, β-H), 3.75, 3.62 (s, 3H, OCH$_3$), 2.98 (s, 3H, NCH$_3$), 2.82, 2.49 (bt, 1H, OH). Anal. Calcd. for: C$_{13}$H$_{17}$O$_5$N: C, 58.42; H, 6.41; N, 5.24. Found: C, 58.29; H, 6.60; N, 5.05.

Methyl-N-(benzyloxycarbonyl)-N-(methyl)-L-serinate-O-(2,3,6,2',3',4',6'-hepta-O-acetyl)-β-D-lactoside, (25b)

Reaction as in (3a→7) above, with 25a and 20 to give 25b after chromatography[31] ($R_f$ 0.41 hexanes/EtOAc 4:6) as a foam (40% ). $[\alpha]^{20}{}_D=-18°$ (c=0.7, CHCl$_3$). Characteristic nmr-data: $^1$H-nmr (CDCl$_3$) δ 7.37-7.26 (m, 5H, aromatic H), 4.534 (d, 1H, H- 1, $J_{1,2}$=7.8 Hz); 4.472 (d, 1H, H-1', $J_{1',2}$=7.7 Hz); 2.15-1.98 (m, 21H, 7 O=CCH$_3$). Anal. Calcd. for $C_{39}H_{51}O_{22}N$: C, 52.87; H, 5.80; N, 1.58. Found: C, 52.94; H, 5.69; N, 1.47.

Methyl-N-(benzyloxycarbonyl)-L-serinate, (26a).

Methyl-L-serinate HCl (2.33g) was suspended in dry $CH_2Cl_2$ (30 mL) and cooled to 0° C. Into this mixture $Et_3N$ (7.5 mL) and benzyloxycloroformate (2.15 mL) were dropped carefully in the same time. The stirring was continued for 16 hrs at room temperature. The reaction mixture was diluted $CH_2Cl_2$ (30 mL) washed by 0.5N HCl solution (3×10 mL), water, dried by $MgSO_4$, filtered and separated on column to give 26a. 2.4 g (63.6%); ($R_f$ 0.35 hexanes/EtOAc 1:1). $^1$H-nmr ($CDCl_3$)δ 7.36-7.26 (m, 5H, aromatic H), 5.79 (bd, 1H, NH), 5.12 (s, 2H, $CH_2$), 4.44 (bm, 1H, α-H), 3.94 (bm, 2H, β-H), 3.77 (s, 3H, $OCH_3$), 2.47 (bt, 1H, OH). Anal. Calcd. for $C_{12}H_{15}O_5N$: C, 56.91; H, 5.97; N, 5.53. Found: C, 56.72; H, 6.09; N, 5.31.

Competition reaction between 3a and 26a.

Two equivalents 3a and 2 eq 26a were treated with 1 eq acetobromoglucose (18) and 1 eq $AgSO_3CF_3$ as described for 22. Orthoester 24 was the only carbohydrate-bearing substance observed in the crude reaction mixture, and was identified by the characteristic signals of $^1$H-nmr spectrum: $^1$H-nmr ($CDCl_3$)δ 7.64-7.18 (m, 10H, aromatic H), 5.61 (d, 1H, −1, $J_{1,2}$=5.2 Hz), 3.71 (s, 3H, $OCH_3$, 2.09, 2.08, 2.04 (3s, 9H, 3 O=$CCH_3$), 1.67 (s, 3H, orthoester $CH_3$).

Methyl-N-(carbobenzyloxy)-L-serinate-O-(2,3,6,2',3',4',6'-hepta-O-acetyl)-β-D-lactoside, (26b)

Reaction as in (3a→7) above, with 26a and 20 to give 26b after chromatography[31] ($R_f$ 0.39 hexanes/EtOAc 4:6) as a foam (18%). Characteristic nmr-data: $^1$H-nmr ($CDCl_3$)δ 7.38-7.26 (m, 5H, aromatic H), 5.79 (broad d, 1H, NH), 4.45 (d, 1H, H-1, $J_{1,2}$=7.9 Hz); 4.43 (d, 1H, H-1', $J_{1',2}$=7.9 Hz), 3.74 (s, 3H, $OCH_3$), 2.15-1.96 (7s, 21H, 7 O=$CCH_3$). Anal. Calcd for $C_{38}H_{49}O_{22}N$: C, 52.35; H, 5.67; N, 1.61. Found: C, 52.51; H, 5.44; N, 1.47.

Methyl-N-(diphenylmethylene)-L-serinate-O-(2,3,4,6-tetra-O-benzyl)-α-D-glucopyranoside, (28)

Schiff base 3a (283 mg, 1 mmol), $nBu_4N+Br^-$ (644 mg, 2 eq.) powdered, oven-dried 4 Å molecular sieves (2.5 g) were stirred in 10 mL dry $CH_2Cl_2$ at RT under argon. After 10 min of stirring, glycosyl donor 27[36] (580 mg, 0.96 mmol), and $iPr_2NEt$ (193 mg, 1.5 eq) were added. After 7 days the ratio of bromosugar to product (2:8) was no longer changing by TLC, and the mixture was diluted with $CH_2Cl_2$ (50 mL), filtered through celite and the organic layer was washed with $H_2O$ (3×15 mL), and dried ($MgSO_4$). Rotary evaporation and flash chromatography[31] ($R_f$ 0.49 hexanes EtOAc/$CH_2Cl_2$ 7:2:1) provided 410 mg of pure 28 as a syrup (53%). $[\alpha]^{20}_D$=+38° (c=0.40, $CHCl_3$). Anal. Calcd. for $C_{51}H_{51}O_8N$: C, 76.00; H, 6.37; N, 1.73. Found: C, 75.83; H, 6.29; N, 1.66.

Methyl-L-serinate-O-α-D-glucopyranoside. HCl, (29)

Glycoside 28 (25 mg) was dissolved in MeOH (5 mL), and HCl (2.6 μl 36%) and 5% palladium on activated carbon (25 mg) were added. The mixture was stirred under $H_2$ (balloon) for 2 hrs, diluted with $CH_2Cl_2$ (20 mL), filtered, and evaporated to give 9.5 mg 29 as an amorphous solid (96%). $[\alpha]^{20}_D$=+21° (c=1.1, $CH_3OH$). Characteristic nmr-data: $^1$H-nmr ($D_2O$) δ 4.72 (d, 1H, H-1, $J_{1,2}$=3.7 Hz), 3.65 (s, 3H, $OC_3$). For $^{13}$C-nmr data, see Table 2 (FIGS. 7a and 7b). Anal. Calcd. for $C_{10}H_{20}O_8NCl$: C, 37.80; H, 6.34; N, 4.41. Found: C, 37.51; H, 6.17; N, 4.18.

Benzyl-N-(diphenylmethylene)-L-serinate-O-(2,3,4,6-tetra-O-benzyl)-O-α-D-glucopyranoside, (30)

Reaction as in (3a→28) above, with Schiff base 3c and glycosy donor 27 to give 30 after chromatography[31] ($R_f$ 0.33 hexane-EtOAc 8:2) as a foam (56%). $[\alpha]^{20}_D$=−17.1° (c=0.9, $CHCl_3$). For $^{13}$C-nmr data, see Table 2 (FIGS. 7a and 7b). Anal. Calcd. for $C_{57}H_{55}O_8N$: C, 77.62; H, 6.28; N, 159. Found: C, 77.91; H, 6.10; N, 1.47.

Methyl-L-serinate-O-2,3,4,6-tetra-O-acetyl-β-D-glucopyranoside, (31)

Glycoside 7 (200 mg) was stirred in THF (4.5 mL) and $CF_3COOH$ (0.5 mL) was dropped into it. After 5 minutes the reaction was complete. The mixture was evaporated, and the residue was dissolved in $CH_2Cl_2$ (50 mL), washed with sat. $NaHCO_3$ (3×10 mL), $H_2O$ (3×10 mL), and dried ($MgSO_4$). Solvent removal provided a syrup which was chromatographed on a short column[31] ($R_f$ 0.61 $CH_2Cl_2$-MeOH 93:7) to provide 135 mg 31 as a syrup (92%) $[\alpha]^{20}_D$=−12° (c=0.4, $CHCl_3$). For $^1$H and $^{13}$C-nmr data, see FIGS. 6a, 6b, 7a and 7b. Anal. Calcd. for $C_{18}H_{27}O_{12}N$: C, 48.10; H, 6.05; N, 3.11. Found: C, 48.27; H, 6.14; N, 3.02.

N-(t-butyloxycarbonyl)-O-(2,3,6,2',3',4',6'-hepta-O-acetyl-β-D-lactosyl)-(1→3)-L-serinyl-L-glycine ethylester, (32)

Solid $Na_2CO_3$ (35 mg), $tBoc_2O$ (62 mg), 5% Pd-C (220 mg) and glycoside 16 (220 mg) were sirred in EtOAc (10 mL) under $H_2$ (balloon) at RT. After 4 hrs the starting material had been consumed, and the H2 was removed by vacuum, the Pd-C was filtered off, and the solution was evaporated chromatographed on a short column[31] ($R_f$ 0.6 hexanes/EtOAc 25:75) to give 180 mg as a syrup (86%). $[\alpha]^{20}_D$=+4.3° (c=1.2, $CHCl_3$). Characteristic $^1$H-nmr data: $^1$H-nmr ($CDCl_3$) δ 4.596 (d, 1H, H-1, $J_{1,2}$=7.8 Hz); 4.502 (d, 1H, H-1', $J_{1',2}$=7.8 Hz), 2.15-1.97 (7s, 21 H, 7 O=$CCH_3$), 1.44 (s, 9H, $C(CH_3)_3$), 1.29 (t, 3H, $CH_2CH_3$). For $^{13}$C-nmr data, see FIGS. 7a and 7b. Anal. Calcd. for $C_{38}H_{56}O_{23}N_2$: C, 50.21; H, 6.21; N, 3.08. Found: C, 49.98; H, 6.16; N, 2.99.

Diphenylmethyl-L-serinate-O-(2,3,4,6-tetra-O-acetyl)-β-D-glucopyranoside, (33)

Glycoside 10 was stirred in THF and $CF_3COOH$ as in (7→31) above, and chromatographed on a short column[31] ($R_f$ 0.41 $CH_2Cl_2$/EtOAc/MeOH 85:10:5) to give 33 (81%) $[\alpha]^{20}_D$=−11.7° (c=0.75, $CHCl_3$). For $^1$H-nmr data, see FIGS. 6a and 6b. Anal. Calcd. for $C_{30}H_{35}O_{12}N$: C, 59.89; H, 5.86; N, 2.32. Found: C, 59.71; H, 5.94; N, 2.22.

L-serine-O-2,3,4,6-te.-a-O-acstyl-β-D-glucopyranoside, (34)

Glycoside 10 (25 mg) and 5% Pd-C (25 mg) were sirred in MeOH (5 mL) under H2 (balloon) at RT. After 1.5 hrs the Pd-C was filtered off, and the residue was evaporated to give 14 mg 34 as an amorphous solid (98%) $[\alpha]^{20}_D$=−15° (c=0.28, MeOH). TLC: $R_f$ 0.48 ($CH_2Cl_2$-MeOH 65:35). For $^1$H and $^{13}$C-nmr data, see FIGS. 6a, 6b, 7a and 7b. Anal. Calcd. for $C_{17}H_{25}O_{12}N$: C, 46.71; H, 5.78; N, 3.06. Found:

C, 46.48; H, 5.70; N, 2.99.

Diphenylmethyl-N-[N-(ter-butyloxycarbonyl)-L-phenylalanyl]-L-serinate-O-(2,3,4,6-tetra-O-acetyl)-β-D-glucopyranoside, (35)

Amino ester glycoside free base 33 (114 mg), HOBT (25.5 mg) and N-α-t-Boc-L-Phe (50 mg) were dissolved in dry THF (5 mL), cooled to 0° C. and DCCl (41 mg) was added. After stirring overnight the precipitate was filtered, and the solution was evaporated. The residue was dissolved in $CH_2Cl_2$ (50 mL) washed with sat. $NaHCO_3$, $H_2O$, dried ($MgSO_4$) and chromatographed on a short column[31] ($R_f$ 0.52 $CH_2Cl_2$/EtOAc 8:2) to give 136 mg 35 as a foam (84%) $[\alpha]^{20}_D = -3.1°$ (c=0.38, $CHCl_3$). Characteristic nmr data: $^1$H-nmr ($CDCl_3$) δ 7.31-7.16 (m, 15H, aromatic H), 6.82 (s, 1H, $CHPh_2$), 2.04-2.00 (4s, 12H, 4 O=$CCH_3$), 1.34 (s, 9H, $C(CH_3)_3$). $^{13}$C-nmr ($CDCl_3$) δ 100.71(C1), 79.86 ( $\underline{C}(CH_3)_3$), 61.53 (C6), 28.06 ($C(\underline{C}H_3)_3$). FAB MS (glycerin matrix) calculated monoisotopic mass of $C_{44}H_{52}O_{15}N_2$ 848.33 m/z 849.25 [MH$^+$].

N-(9-Fluorenylmethoxycarbonyl)-L-serine-O-(2,3,4,6-tetra-O-acetyl)-β-D-glucopyranoside, (36)

Amino acid glycoside 34 (331 mg) was stirred in a mixture of 10% $NaHCO_3$ in water (5 mL) and dioxane (3 mL) at 0° C. Fmoc-Cl (197 mg) in dioxane (3 mL) was added over 30 min. After stirring at 0° C. for 4 hrs and then RT for 8 hrs, the reaction mixture was evaporated, dissolved in $CH_2Cl_2$ (60 mL), washed with $H_2O$ (3×10 mL), dried, evaporated, and chromatographed[31] ($R_f$ 0.67 $CH_2Cl_2$/MeOH 8:2) to give 295 mg 36 as an foam (92%). $[\alpha]^{20}_D = +25°$ (c - 0.4, $CHCl_3$). Characteristic nmr-data: $^1$H-nmr ($CDCl_3$) δ 7.79-7.26 (m, 8H, aromatic H), 5.66 (bd, 1H, NH), 4.51 (d, 1H, H-1, $J_{1,2}$=7.1 Hz), 3.66 (ddd, 1H, H-5), 2.09-2.01 (4s, 12H, 4 O=$CCH_3$). Anal. Calcd. for $C_{32}H_{35}O_{14}N$: C, 58.44; H, 5.36; N, 2.12. Found: C, 58.30; H, 5.44; N, 2.01.

$H_2$N-Tyr-D-Cys-Gly-Phe-D-Cys-Ser(O-β-D-Glc)-Gly-CONH$_2$, (38)

Peptide assembly via Fmoc chemistry was performed manually (0.85 g scale, 10 mL wash volumes), starting with 4-(2',4'-dimethoxyphenyl-Fmoc-aminomethyl)phenoxy resin (Rink's [18a] Resin-Bachem California, Torrance, Calif.) (0.46 mmol/g). Fmoc removal was accomplished with piperidine/DMF (3:7, 3×10 min), followed by washing with DMF (6×1 min). Couplings were achieved by adding the reagents sequentially to the resin in order: 1.5 eq Fmoc amino acid, 15 eq BOP reagent, 1.5 eq HOBT, and 2.5 eq $iPr_2$NEt. The mixture was agitated by bubbling argon through the reaction mixture (frit) for 1-2 hrs (negative ninhydrin test obtained). Upon completion of chain assembly, Fmoc group was removed as above. The acetyl protecting groups for the glucoside moiety were removed with $H_2NNH_2$•$H_2O$/MeOH (4:1, 2 hrs) while the peptide remained anchored to the resin. The excess $H_2NNH_2$ was washed with MeOH (4×1 min) and $CH_2Cl_2$ (4×1 min). The cleavage was carried out with $CF_3COOH/CH_2Cl_2/H_2O$ (8:16:1, 100 mL), which also removed the t-butyl ether from the side chain of the tyrosine. The filtrate was diluted with $H_2O$ (100 mL), and vacuum distilled at 25° C. to a volume of 100 mL. After lyophilization the crude glycopeptide was dissolved in water (20 mL), the acidity, was adjusted to pH=4 with AcOH, and Hg(OAc)$_2$ (140 mg) was added. After stirring for 75 min the reaction was diluted with $H_2O$ (180 mL) and treated with $H_2S$. The HgS precipitate was and removed by filtration, and excess $H_2S$ was purged with a stream of $N_2$. The peptide was oxidized with aqueous $K_3Fe(CN)_6$(312 mg in 1000 mL $H_2O$) while the acidity was kept constant (pH=8.4) with $NH_4OH$. After 10 hours the acidity was adjusted to pH=4 with AcOH, and Amberlite® 68 resin (Cl$^-$ form) was added, and the reaction was stirred until the yellow color disappeared. After filtration the reaction was lyophilized and purified by HPLC ($t_R$=24.9 min, 0–50% MeCN in 0.1% aqueous TFA in 50 min, $C_{18}$ column) to provide enkephalin analogue 38 in 28% yield, based on resin. Characteristic $^1$H-nmr data: $^1$H-nmr ($D_2O$) δ 7.33-7.23 (m, 5H, Phe aromatic H), 7.12, 6.84 (dd, 4H, Tyr aromatic H), 4.40 (d, 1H, H-1, $J_{1,2}$=7.8 Hz). FAB MS (glycerol matrix) calculated monoisotopic mass of $C_{37}H_{50}O_{14}N_8S_2$ 894.28 m/z 895.56 [MH$^+$] observed.

B. Creation of Nucleophilic Serine and Threonine Schiff Bases and Synthesis of β-Glycosides via the Hanessian Modification of the Koenigs-Knorr Procedure.

The required serine and threonine ester Schiff bases (3a-c, 4a, 4b, and 5 shown in FIG. 2) were prepared from diphenylketimine (benzophenone imine) and the appropriate α-amino ester hydrochloride salts or tosylate salts using the standard methodology published by O'Donnell and Polt[25, 27]. The benzhydryl ester was chosen for carboxyl protection because of its easy hydrogenolysis, and because its steric bulk affords greater protection than benzyl or allyl. All of the compounds in FIG. 2 were crystalline. Solution $^1$H- and $^{13}$C-nmr studies indicated that each β-hydroxy Schiff base exists in a tautomeric equilibrium with the cyclic oxazolidine form. X-ray analysis of 4a showed that it had crystallized as the oxazolidine structure.[26] With the exception of the extremely unhindered electrophile Ph—N=C=O,[27] we have always observed reaction at the oxygen[28] of the open-chain β-hydroxy imine tautomer with a variety of electrophiles-including glycosyl donors.

Figure 3:
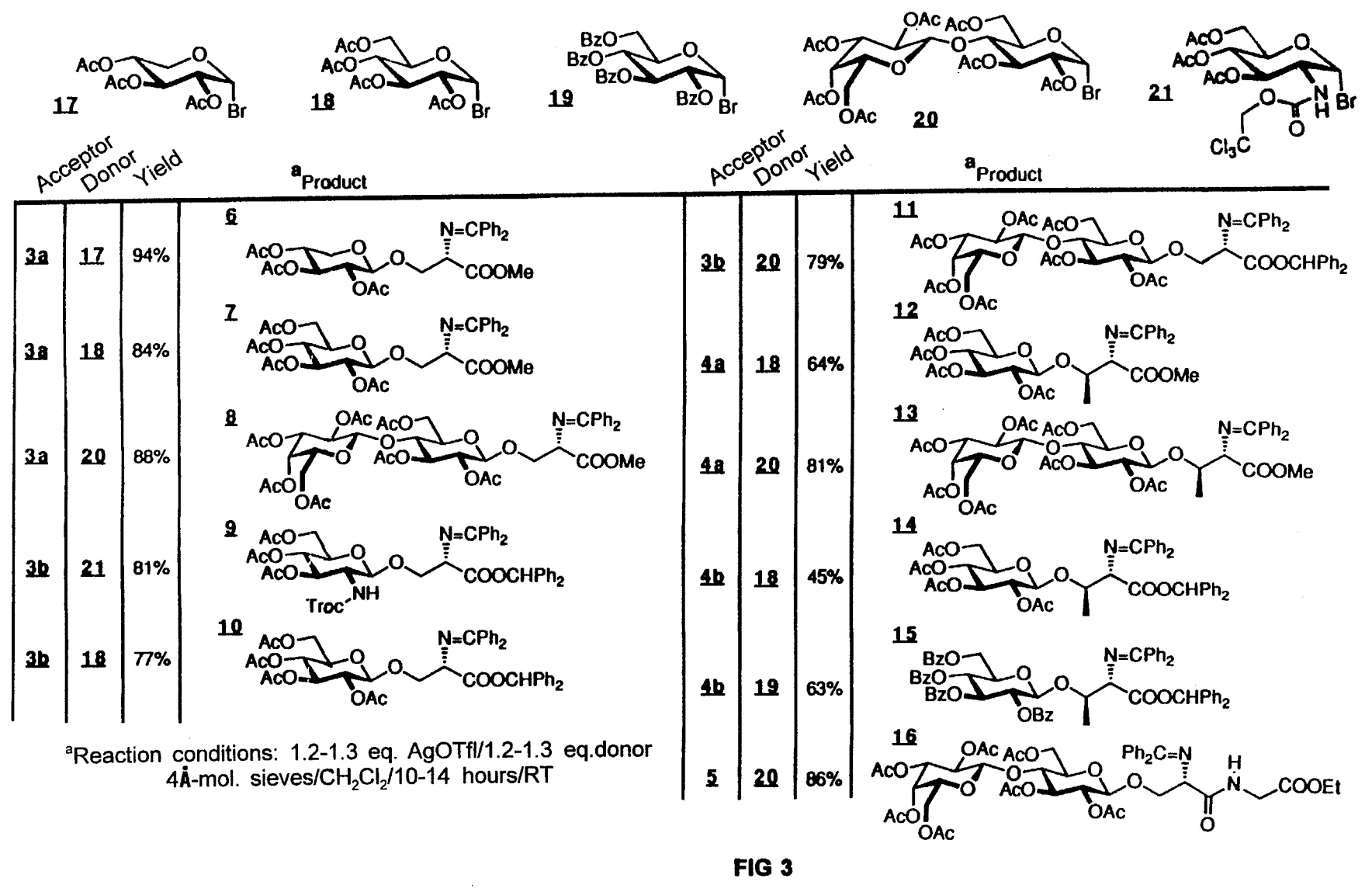

Glycosylation of the β-hydroxy Schiff bases with "participating" glycosyl donors was straightforward and gave the 1,2-trans products (β-glycosides). Although Helferich's glycosylation method[29] (Hg(CN)$_2$/PhCH$_3$-CH$_3$NO$_2$) worked well, Hanessian's modification of the Koenigs-Knorr reaction[30] was superior. Thus, the Schiff bases 3–5 were treated with various acyl-protected glycosyl bromides 17–21 in $CH_2Cl_2$ at room temperature for several hours with AgOTfl as a promoter to provide the desired β-glycosides 6–16 in good to excellent yield. FIG. 3 shows the different combinations of acceptors and donors and the product that was produced. The product glycosides were purified on $SiO_2$ by flash chromatography,[31] and the corresponding 1,2-cis products (α-glycosides) could not be detected by either 250 MHz $^1$H-nmr, or by thin-layer chromatography.

There is some diminution in yield as the steric bulk of the glycosyl acceptor is increased (Ser→Thr and COOMe→COOCHPh$_2$), thus 4b is significantly less reactive than 3a (c.f. 45% yield of 14 vs 84% yield of 7). Use of a more, reactive glycosyl donor, such as per-benzoate 19 partially offsets this diminished reactivity (c.f. 63% yield of 15). The dipeptide Schiff base 5 is quite reactive, in spite of the potentially "unfavorable" H-bond between the amide N—H and the hydroxyl which has been observed in small threonine- and serine-containing peptides.[33]

Figure 4:
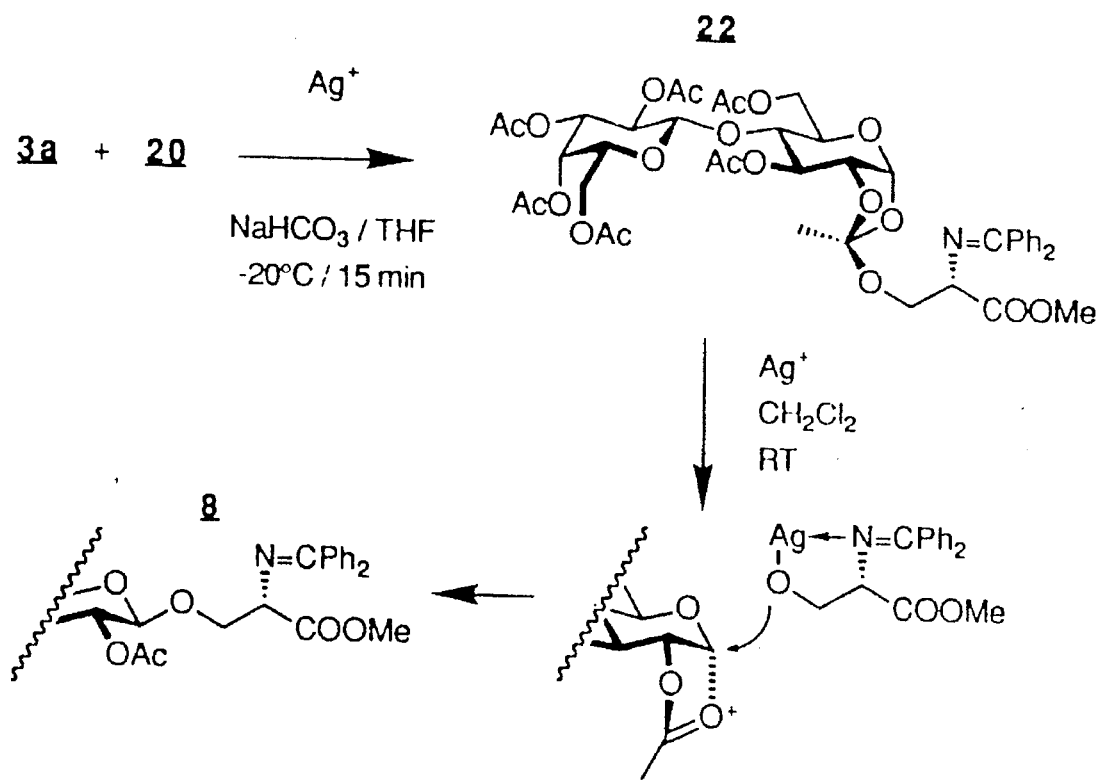
FIG. 4 describes the isolation of orthoesters.

Small amounts of the corresponding orthoesters were isolated from the reaction mixtures, and when the glycosylation reactions were run in THF with solid $NaHCO_3$ as a buffer, orthoesters (12a, 22–24) were isolated in excellent yield after 5–10 minutes at −20° C. When the crystalline orthoester 22 was treated with AgOTfl, HgBr$_2$, or Me$_3$SiOTfl in CH$_2$Cl$_2$, glycoside 8 was obtained in high yield (FIG. 4), suggesting that the orthoesters are indeed reaction intermediates in the Koenigs-Knorr reaction as independently proposed by Garegg and by Schroeder, inter alia.[32]

Figure 5:
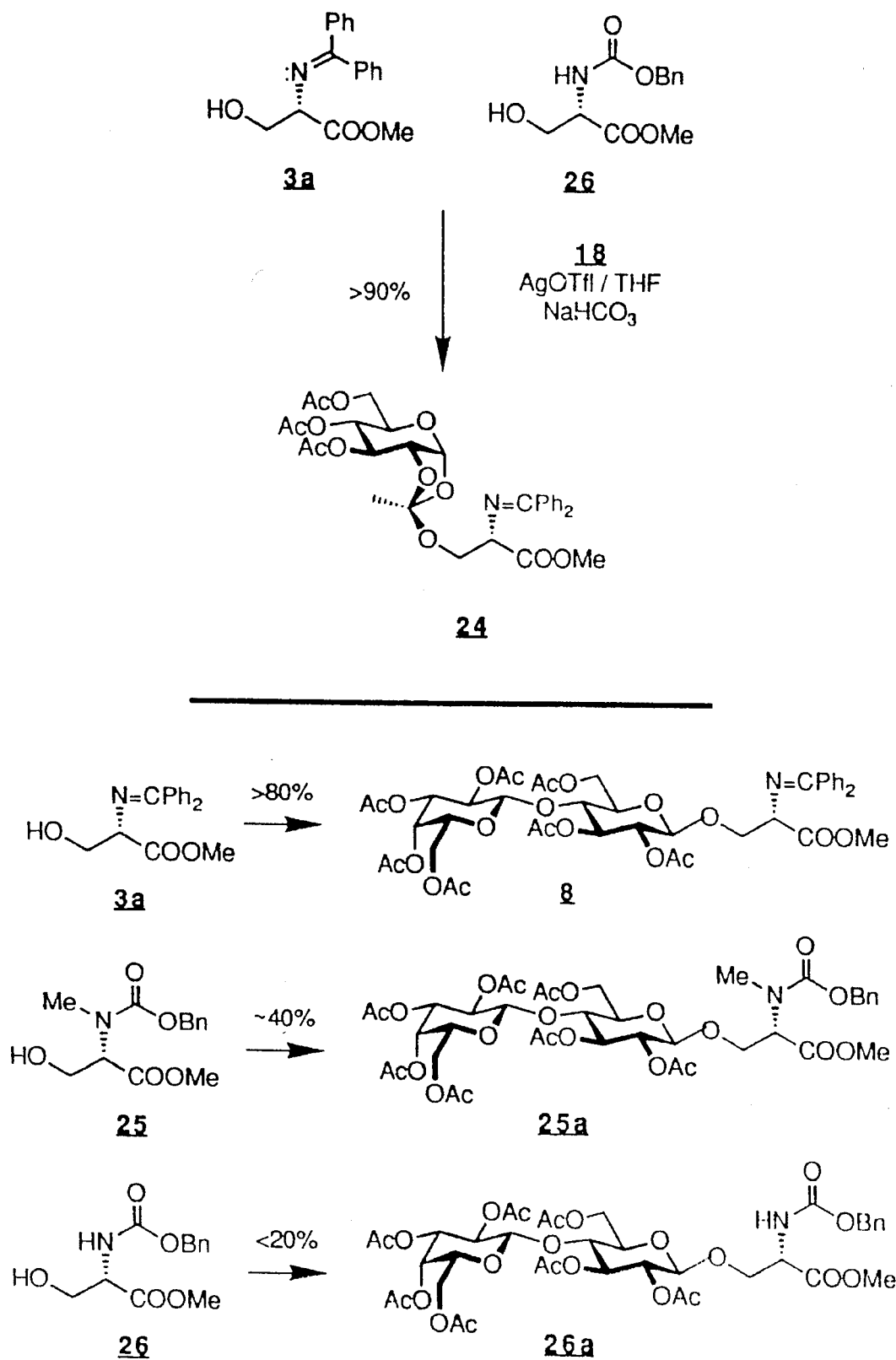
FIG. 5 describes an experiment performed to examine whether benzophenone-protected α-imino esters are more nucleophilic than Cbz-protected α-amido esters, and to examine the reactivity of 3a, 25a, and 26a with acetobromoglucose and AgOTfl.

FT-IR measurements of 3a in dilute CHCl$_3$ solution show a sharp O—H stretching peak which is shifted ($\Delta V_{OH}$) from the expected value by approximately 340 cm$^{-1}$ to lower wave numbers. This is consistent with a strong intramolecular hydrogen bond.[34] Several experiments were performed to see if the benzophenone protected α-imino esters (favorable H-bond, c.f. 3a) are in reality more nucleophilic than the Cbz-protected α-amido esters (unfavorable H-bond, c.f. 26a), and to examine the hydrogen bonding hypothesis (FIG. 5). In competition experiments, two eq. each of glycosyl acceptors 3a and 26a were allowed to react with one eq. of acetobromoglucose for 15 minutes at 0° C. in THF in the presence of one eq. AgOTfl and excess solid NaHCO$_3$. Orthoester 24 was the only coupling product observed in crude reaction mixtures by 250 MHz $^1$H-nmr, and was isolated in over 90% yield. One explanation of the increased reactivity of 3a is that the intramolecular hydrogen bond in 3a increases the electron density on the hydroxyl group, thereby increasing the nucleophilicity of the oxygen; whereas the hydrogen bonding in 26a serves to remove electron density from the hydroxyl, thereby decreasing the nucleophilicity of the oxygen.

A plausible alternative explanation is that the bidentate β-hydroxy imine 3a may coordinate to Ag$^+$ (or Hg$^{++}$ in the case of the Helferich reaction[29]), causing a proximity effect[35] which favors the reaction of 3a with the glycosyl donor. Both of these arguments are consistent with Garegg's suggestion[32c] that increasing basicity of the glycosyl acceptor increases the rate in the Koenigs-Knorr reaction. Since the bidentate Schiff bases are much more basic than a typical primary alcohol, the nucleophilicity of the glycosyl acceptor is increased, as well as the basicity of the intermediate orthoester which must undergo proton or metal-catalyzed rearrangement to thr β-glycoside product.

In three separate experiments (FIG. 5), the reactivity of 3a, 25a, and 26a with acetbromoglucose 18 and AgOTfl was compared using Hanessian's method.[30] The result of each experiment is in agreement with the hydrogen bonding hypothesis: that is, 3a (favorable H-bonding) provided a high yield (>80%) of glycoside; 26a (unfavorable H-bonding) provided a low yield (<20%); and 25a (no H-bonding) provided an intermediate yield of the glycoside ($\cong$40%). Thus, while we cannot rule out other effects (i.e. chelation of the Ag$^+$ promoter and/or basicity of the hydroxyl), hydrogen bonding of the glycosyl acceptor certainly plays an important role in glycosylation reaction rates,[20] as well as other related reactions between electrophiles and alcohols.[22]

All of the $^1$H-nmr chemical shift assignments (δ) and most of the coupling constants (HZ) for the β-glycoside products were provided by COSY, and are listed in FIGS. 6a and 6b. The $^{13}$C-nmr chemical shift assignments (δ) are listed in FIGS. 7a and 7b. All of our $^{13}$C-nmr data were consistent with published data on glycosides,[51] which was very helpful in making the correct assignments. It should be noted that the N-methyl amino acid derivative 25 shows two rotomer populations in the $^{13}$C-nmr spectrum, as might be expected for a 3° amide structure.

C. Synthesis of α-Linked Glycosides via Lemieux's in situ Anomerization Method.

Figure 8:
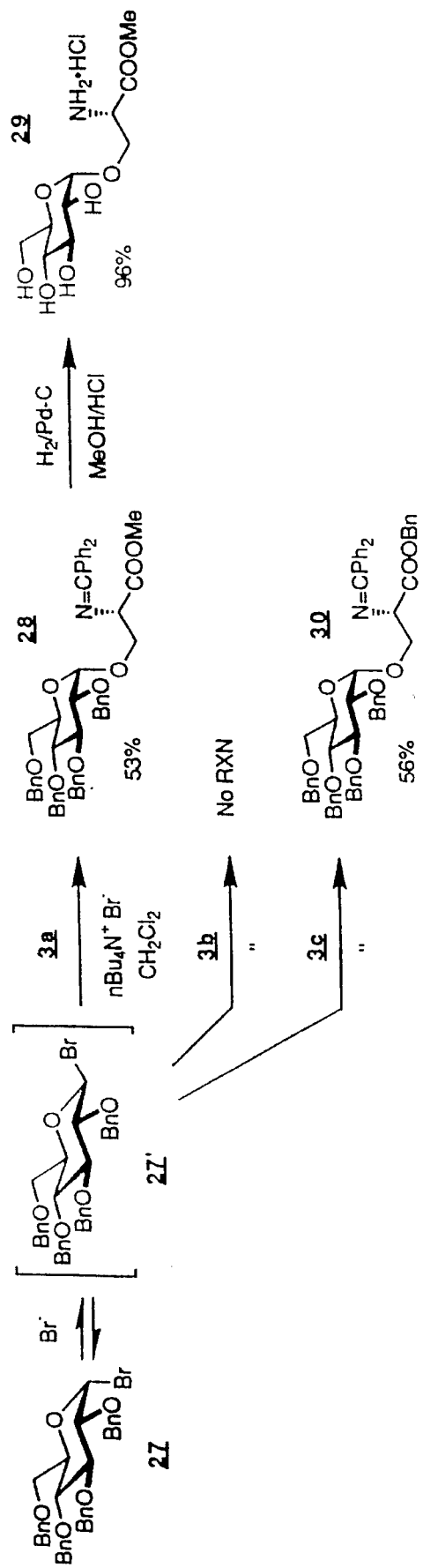
FIG. 8 is a flow chart describing the creation of an amino acid glycoside using Lemieux's anomerization method.

Lemieux's in situ anomerization method[36] (nBu$_4$N$^+$Br$^-$/iPr$_2$NEt/CH$_2$Cl$_2$) was applied to 3a using the per-benzylbromoglucose 27[36] as a glycosyl donor (FIG. 8). Presumably, the equatorial anomer 27 is the reactive species. While the relatively unhindered methyl ester 3a provided a 53% yield of α-glycoside 28, the more sterically hindered benzhydryl ester 3b completely failed to react. This is due to the increased steric demand of the S$_N$2-like transition state of the Lemieux conditions, coupled with the 1,3-diaxial interactions generated by the approach of the glycosyl acceptor. The Koenigs-Knorr transition state shows less sensitivity to steric hindrance because of the equatorial approach of the nucleophile, and the increased S$_N$1-character. Attempts to force the Lemieux reaction to completion by adding DMF or warming the reaction resulted in elimination of HBr from the glycosyl donor to form the benzylated glucal. The less-hindered benzyl ester 3c reacted with 27 under identical conditions to provide the α-glycoside 30 in 56% yield. In both cases, only small amounts (~20:1) of the corresponding β-products could be observed in the $^1$H-nmr of the crude reaction mixtures of glycosides 28 and 30.

D. Hydroxyl, Amino, and Carboxyl Deprotection And Solution-Phase Coupling of the Amino Acid Glycosides.

Figure 9:
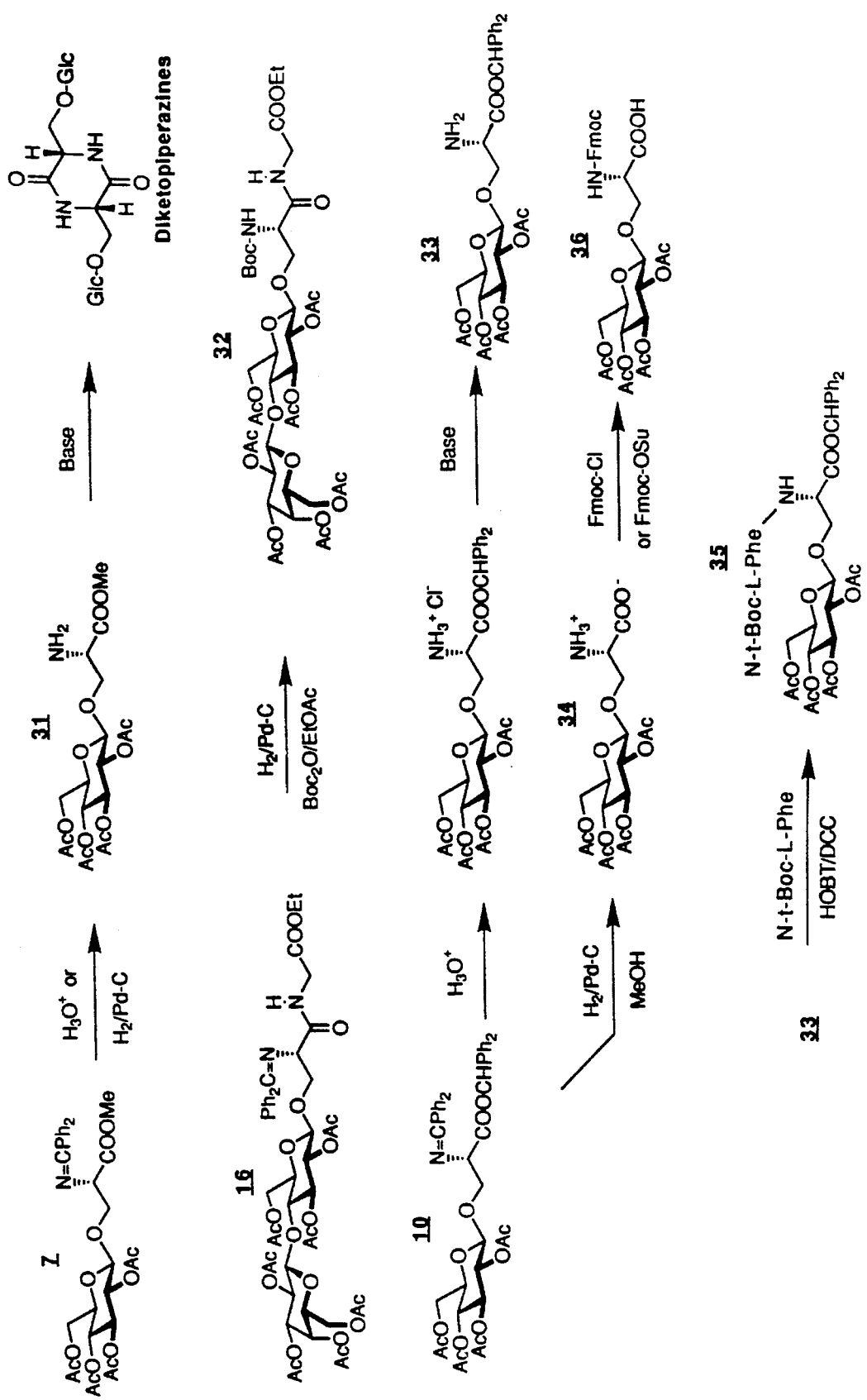
FIG. 9 is a flow diagram demonstrating solution phase coupling of amino acid glycosides.

The synthesis of O-linked glycopeptides requires protecting groups which can be removed under neutral, mildly acidic, or mildly basic conditions.[17] While the —OH, —NH$_2$, and —COOH protecting groups used in this study cannot be removed in a completely orthogonal manner,[37] the sterically hindered Ph$_2$C=N-moiety does provide several convenient routes for deprotection (FIG. 9). Treatment of Schiff base glycosides with mild aqueous acid (e.g. 0.1–1.0N. aq. HCl/Et$_2$O or THF, or 5% citric acid) at 0° or RT for several hours provided the amino ester glycosides as free bases, or as the HCl salts.[1,25] Similarly, acid-catalyzed hydrolysis (1.05–1.20 eq. CF$_3$COOH in) of the imine moiety of glycosides 7 and 10 also facilitated the selective removal of the amino-protecting group in moist (1–2% water) CH$_2$Cl$_2$ or THF gave 31 and 33, as did two equivalents TsOH.H$_2$O in THF. As free bases, the more hindered benzhydryl amino esters[38] (e.g. 33) were more stable than their methyl ester counterparts which formed diketopiperazines under basic conditions. Hydrogenolysis of 16 in the presence of di-tert-butylpyrocarbonate (Boc$_2$O) and solid NaHCO$_3$ provided the Boc-protected amino ester 32. Simultaneous hydrogenolysis (1 atm. H$_2$/5–10% Pd-C/MeOH) of the —N=CPh$_2$ and —OCHPh$_2$ groups from 10 provided the glycosyl amino acid 34 in excellent yield. Similarly, the benzyl groups used for protection of —OH in the Lemieux procedure could be removed by hydrogenolysis, simultaneously with the Schiff base (c.f. Scheme 5 28→29). Deacylation of the blocked sugar moieties could not be accomplished using Zemplèn conditions[39] (cat. NaOMe/MeOH) without first removing the Schiff base, which has an acidifying effect on the α-hydrogen of the amino acid residue,[40] thus promoting retro-Michael addition of the glycoside.

Solution-phase amino acid coupling of the protected amino ester glycosides proceeds without difficulty (FIG. 9). Thus, protected dipeptide glycoside 35 was synthesized in 84% yield from 34 and Boc-L-Phe using classical HOBT/DCC methodology.[41] Once the amino terminus has been acylated, either with Boc, Z (Cbz), or another amino acid residue, one can remove the acetate groups which protect the hydroxyls using the classical Zemplèn procedure[39] with no diketopiperazine formation (c.f. FIG. 9).

E. Solid Phase Coupling, Deprotection and Cleavage of O-Linked Glycopeptides and Synthesis of A Potent O-Glycosyl DPDPE Analogue.

Workers attempting solid-phase glycopeptide synthesis have been hampered by three intrinsic problems: 1) Deprotection of the growing peptide chain; 2) Removal of the hydroxyl protection on the carbohydrate moiety; and 3) Cleavage of the completed glycopeptide from the support resin. These problems are especially acute when synthesizing O-linked glycopeptides which are base-labile at the serine or threonine residue, in addition to the normal acid-sensitivity shown by the glycosidic acetals.

Figure 10:
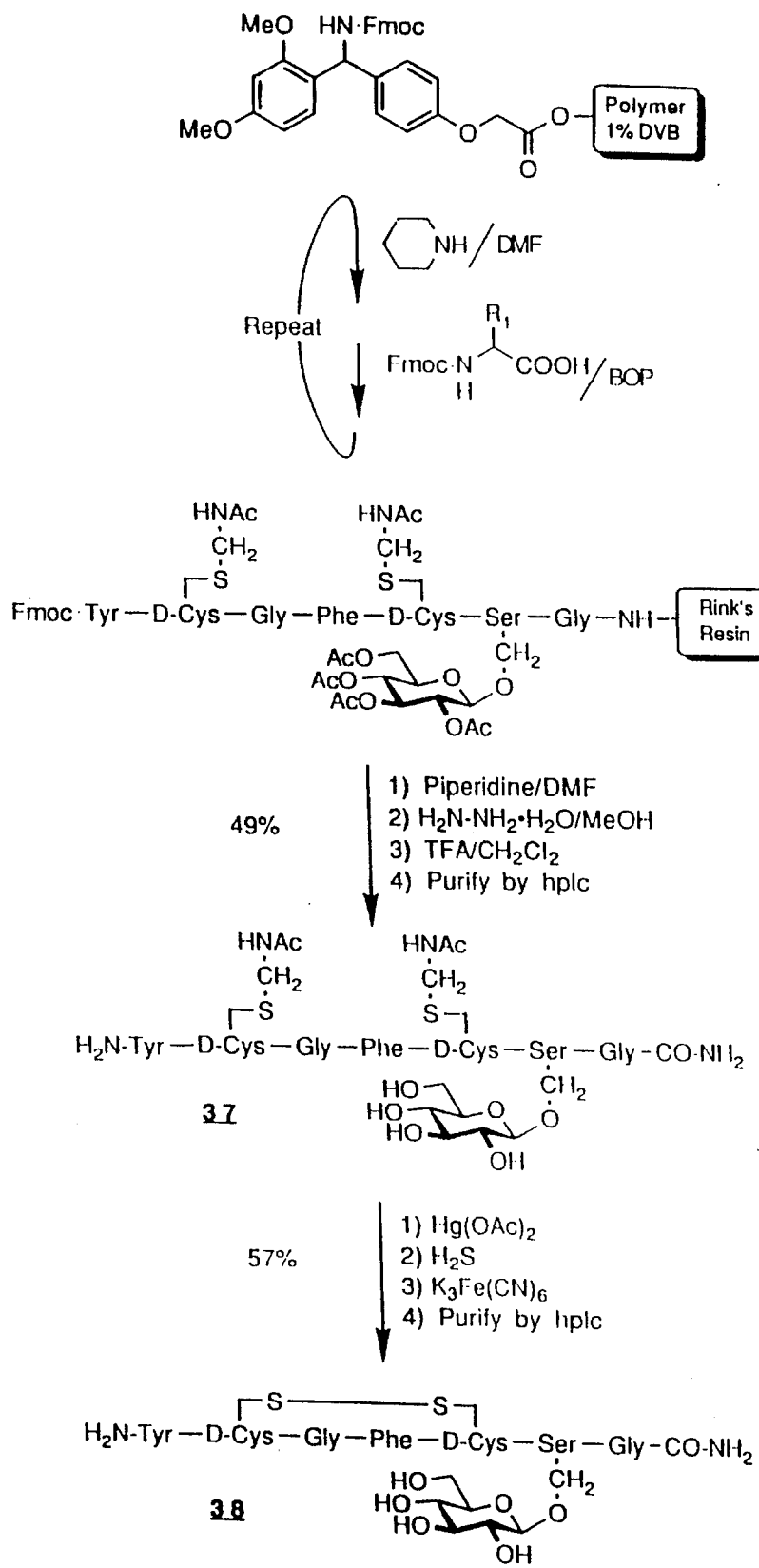
FIG. 10 is a flow diagram demonstrating solid phase coupling of amino acid glycosides.

The Fmoc-based peptide methodology is ideally suited to glycopeptide synthesis[42] since the deprotection step (piperidine/DMF) is compatible with most hydroxyl protecting groups commonly used in polysaccharide constructions. Step-wise or simultaneous removal of the —OCHPh$_2$ and Ph$_2$C=N— groups from 10 as described previously, followed by re-protection of the amino group with Fmoc-Cl or Fmoc-OSu[19] (FIG. 9) provided protected glycosyl amino acid 36, suitable for solid phase coupling using Castro's BOP reagent.[43] The coupling strategy is depicted in FIG. 10. Because Fmoc-protected serine glycosides (c.f. 36) are much more sterically encumbered than the typical proteogenic amino acids normally encountered in solid-phase peptide synthesis, it was not surprising that coupling of the carbohydrate-bearing residue was slower (~4 hrs) than usual. The following coupling to the terminal glucosyl-bearing serine was normal, as were subsequent couplings. When 36 was coupled directly to the resin, extended reaction times (>24 hrs) were required, and acylation was never complete. Apparently, some of the acylation sites on the resin were not available to the bulkier glycosyl Fmoc-amino acid. Acetamidomethyl[44] groups were used to protect the sulfhydryl groups of the Fmoc-cysteine residues. The t-butyl group was used for protection of the tyrosine hydroxyl, but was not required for coupling. Deprotection of the amino termini with piperidine in DMF was accomplished in the normal fashion after each coupling step.[19]

Removal of acetate groups from the carbohydrate portion of O-linked glycopeptides is still a particularly vexing problem since the usual basic conditions used for removal[39] lead to loss of the carbohydrate.[17] We utilized a procedure developed by Kunz[45] that relies on aqueous hydrazine in MeOH to remove the acetates nucleophilically. Since the glycopeptide was still bound to the support at this stage, separation of the soluble acethydrazide byproduct was accomplished by simply washing the resin with CH$_2$Cl$_2$.

Due to the presence of the acid-labile O-glycoside, an extremely acid-sensitive trialkoxybenzhydryl-type linkage was required for efficient cleavage of the deprotected glycopeptides from the polymer support. Because we required a carboxamide C-terminus on the enkephalin analogues, we chose the benzhydrylamine-functionalized polystyrene developed by Rink[18] as a support. Thus, cleavage with TFA-CH$_2$Cl$_2$ provided 200 mg of the desired 1° amide glycopeptide 37 with concomitant cleavage of the t-butyl group on tyrosine. After cleavage from the polymer support, the sulfhydryl-protecting acetamidomethyl groups were removed with Hg$^{++}$[44], and the disulfide bond was formed with K$_3$Fe(CN)$_6$ in dilute aqueous solution[46] to provide the biologically active[47] enkephalin analogue 38. The overall yield, based on the resin was 28%. FAB-MS and $^1$H-nmr indicated that the β-glucoside had been retained, and that no detectable anomerization had occurred during deprotection and cleavage of the peptide from support. A series of glycosylated enkephalin analogues have been prepared using this methodology.[47]

---

SEQUENCE LISTING ( 1 ) GENERAL INFORMATION:

( i i i ) NUMBER OF SEQUENCES: 1

( 2 ) INFORMATION FOR SEQ ID NO:1:

( i ) SEQUENCE CHARACTERISTICS:
      ( A ) LENGTH: 6 amino acids
      ( B ) TYPE: amino acid
      ( D ) TOPOLOGY: linear ( i i ) MOLECULE TYPE: peptide ( x i ) SEQUENCE DESCRIPTION: SEQ ID NO:1:

Val  Thr  His  Pro  Gly  Tyr
   1                    5

---

References.

1. Szabó, L., et al. Tetrahedron Lett. 1991, 32, 585–588.
2. Eylar, H. J. Theoret. Biol. 1965, 10, 89–112.
3. a) Maeji, et al., Biopolymers 1987, 26, 1753–1767,
   b) Hollosi, et al., Biopolymers 1990, 29, 1549–1564,
   c) Paulsen, et al., Carbohydr. Res. 1991, 214, 227–234,
   d) Dill, et al., Carbohydr. Res. 1982, 108, 31–40,
   e) Shogren, et al., Biochemistry 1989, 28, 5525–5536,
   f) Gerken, et al., Biochemistry 1989, 28, 5536–5543. For a general discussion of protein folding, see: g) Dyson, et al., J. Mol. Biol. 1988, 201, 161–200.
4. Winterburn, et al., Nature (London) 1972, 236, 147–151.
5. Montreuil, J., Adv. Carbohydr. Chem. Biochem. 1980, 37, 157–223.
6. Mohr, H. in Reductionism and Systems Theory in the Life Sciences; P. Hoynigen-Huene and F.M. Wuketils (eds.); Kluwer Academic Publishers, Dordrecht, NL, 1989; pp 137–159.
7. For reviews of general methods for glycoconjugate synthesis, see: a) Paulsen, H., Angew. Chem. Int. Ed. Engl. 1990, 29, 823–839, b) Kunz, H., Angew. Chem. Int. Ed. Engl. 1987, 26, 294–308, c) Schmidt, R.R., Angew. Chem. Int. Ed. Engl. 1986, 25, 212–235, d) Garg, et al., Adv. Carbohydr. Chem. Biochem. 1985, 43, 135–201, e) Paulsen, H., Angew. Chem. Int. Ed. Engl. 1982, 21, 155–224, f) Gigg, J., Topics in Current Chemistry 1990, 154, 77.
8. Hollósi, et al., Tetrahedron Lett. 1991, 32, 1531–4.
9. a) Kinzy, et al., Carbohydr. Res. 1987, 166, 265, b) Nakahara, et al., T. Carbohydr. Res. 1991, 216, 211–225, c) Iijima, et

-continued

References.

al., T. Carbohydr. Res. 1989, 186, 107, d) Kunz, et al., Angew. Chem. Int. Ed. Engl. 1987, 25, 360–362.
10. Jansson, et al., Tetrahedron Lett. 1990, 31, 6991–4.
11. Lüning, et al., J. Chem. Soc. Chem. Commun. 1989, 1267–8.
12. a) Lavielle, et al., Carbohydr. Res. 1981, 89, 229–236, b) Lavielle, et al., Biochem. Biophys. Res. Commun. 1979, 91, 614–622.
13. Filira, et al., J. Peptide Protein Res. 1990, 36, 86–96.
14. a) Bardaji, et al., Angew. Chem. Int. Ed. Engl. 1990, 29, 291-2, b) Bardaji, et al., Chem. Soc. Perkin Trans. I 1991, 1755-9.
15. Friedrich-Bochnitschek, et al., J. Org. Chem. 1989, 54, 751–6.
16. Peters, et al., Tetrahedron Lett. 1991, 32, 5067–5070.
17. a) Wakabayashi, et al., Carbohydr. Res. 1974, 35, 3, b) Garg, et al., Carbohydr Res. 1976, 49, 482, c) Vercellotti, et al., Carbohydr. Res. 1967, 5, 97, d) Lacombe, et al., Chem. 1983, 48, 2557–2563.
18. a) Rink, H. Tetrahedron Lett. 1987, 28, 3787–3790, b) Elofsson, et al., Tetrahedron Lett. 1991, 32, 7613-6, c) Albericio, et al., J. Org. Chem. 1990, 55, 3730.
19. a) Carpino, et al., J. Org. Chem. 1972, 37, 3404, b) Paquet, et al., J. Org. Chem. 1982, 60, 976.
20. a) Schmidt, et al., Tetrahedron Lett. 1986, 27, 481-4, b) Ito, et al., Am. Chem. Soc. 1989, 111, 8508, c) Nicolaou, et al., Carbohydr. Res. 1990, 202, 177.
21. a) Micheel, et al., Chem. Ber. 1958, 91, 673, b) Kochetkov, et al., Akad. Nauk. SSSR, Ser. Khim. 1965, 1698, c) Derevitskaya, et al., Carbohydr. Res. 1967, 3, 377, d) Kochetkov, et al., Akad. Nauk. SSSR, Ser. Khim. 1969, 2509, e) Garg, et al., Carbohydr. Res. 1976, 52, 246, f) Jacquinet, et al., Carbohydr. Res. 1974, 32, 137, g) Egan, et al., Carbohydr. Res. 1972, 23, 261, h) Vercellotti, et al., Org. Chem. 1966, 31, 825, i) Garegg, et al., Carbohydr. Res. 1976, 52, 235, j) Lacombe, et al., Can. J. Chem. 1981, 59, 473–481, k) Higashi, et al., Chem. Pharm. Bull. 1990, 38, 3280-2.
22. a) Denis, et al., J. Org. Chem. 1990, 55, 1957, b) Bochkov, et al., The Chemistry of O-Glycosidic Bond: Formation & Cleavage; Pergamon Press, Oxford; 1979; pg 100, and references therein.
23. a) Mosberg, et al., Proc. Natl. Acad. Sci. U.S.A. 1983, 80, 5871-4, b) Hruby, et al., Am. Chem. Soc. 1988, 110, 3351.
24. a) Hruby, V.J. in NIDA Monograph Series: Opioid Peptides: Medicinal Chemistry; Rapaka, R.S.; Barnett, G.; Hawks, R.L., Eds.; National Institute of Drug Abuse, Rockville, MD; 1986, b) For a comprehensive review, see: Hruby, V.J.; Gehrig, C.A. Med. Res. Rev. 1989, 9, 343–401.
25. O'Donnell, et al., Chem. 1982, 47, 2663–2666.
26. a) Wijayaratne, et al., Acta Cryst. B 1992, in press, b) Belokon, et al., J. Am. Chem. Soc. 1985, 107, 4252, c) Garner, et al., J. Org. Chem. 1988, 53, 4395.
27. Polt, et al., J. Org. Chem. 1992, in press.
28. Polt, et al., Tetrahedron Lett. 1992, 33, 2961-4.
29. a) Helferich, et al., K. Chem. Ber. 1956, 89, 314, b) Helferich, et al., J. Chem. Ber. 1962, 95, 2604.
30. Hanessian, et al., J. Carbohydr. Res. 1977, 53, C13.
31. Still, et al., J. Org. Chem. 1978, 43, 2923-5.
32. a) Garegg, et al., Acta Chem. Scand. B 1976, 30, 655-8, b) Wallace, et al., J. Chem. Soc. Perkin II 1977, 795–802, c) Garegg, et al., Acta Chem. Scand. B 1985, 39, 569–577, d) Banoub, et al., Can. J. Chem. 1979, 57, 2091.
33. a) Aubry, et al., Int. J. Peptide Protein Res. 1984, 23, 113–122, b) Siemion, et al., Int. J. Peptide Protein Res. 1986, 27, 127.
34. Aaron, H.S. Top. Stereochem. 1979, 11, 1.
35. Beak, et al., Acc. Chem. Res. 1986, 19, 356.
36. Lemieux, et al., J. Am. Chem. Soc. 1975, 97, 4056.
37. Polt, R.; Qian, X. unpublished results.
38. Aboderin, et al., J. Am. Chem. Soc. 1965, 87, 5469.
39. Szurmai, et al., Carbohydrate Res. 1987, 164, 313.
40. O'Donnell, et al., J. Am. Chem. Soc. 1988, 110, 8520–8525.
41. a) König, et al., Chem. Ber. 1970, 103, 788, b) Bodanszky, et al., The Practice of Peptide Synthesis; Springer-Verlag. Berlin, 1984; pp 143–150.
42. Bardaji, et al., Angew. Chem. Int. Ed. Engl. 1990, 29, 291–292.
43. Rivaille, et al., Tetrahedron 1980, 36, 3413.
44. Veber, et al., J. Am. Chem. Soc. 1972, 94, 5456–5461.
45. Schultheiss-Reimann, et al., Angew. Chem. Int. Ed. Engl. 1983, 1, 62–63.
46. Hruby, et al., J. Med. Chem. 1991, 34, 1823–1830.
47. DPDPE analogue, β-O-glucosyl-ser$^6$-gly$^7$-DCDCE (38) was shown to be active in GPI and MVD opioid assays, and whole rat brain radioligand binding assays (IC$_{50}$'s were 26 nM/&-receptor, and 53 nM/μ-receptor): Hruby, et al., unpublished results.
48. Newth, et al., J. Chem. Soc. 1953, 2904–2909.
49. Fischer, E. Ber. 1927, 60, 1955.
50. Higashi, et al., Chem. Pharm. Bull. 1990, 38, 3280–3282.
51. a) Bock, et al., Adv. Carbohydr. Chem. Biochem. 1983, 41, 27–66, b) Dill, et al., Adv. Carbohydr. Chem. Biochem. 1985, 43, 1-49, c) Banoub, et al., Can. J. Chem. 1979, 57, 2085–2090.
52. Kochetkov, et al., Tetrahedron 1967, 23, 693–707.
53. Fisher, et al. J. Med. Chem 1991, 34, 3140–3143.

We claim:

1. A compound of the formula

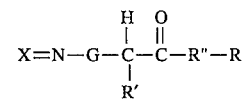

wherein X is an imino-bonded moiety selected from the group consisting of an imine, a Schiff's base, and an imidate ester;

wherein G is a carbon chain of 0–10 carbons;

wherein R is selected from the group consisting of phenyl and diphenyl groups;

wherein R' is selected from the group consisting of groups containing a hydroxyl moiety, groups containing a protected hydroxyl moiety, and groups containing an O-linked sugar; and wherein R" is an amino acid chain having no more than thirteen amino acids.

2. The compound of claim 1 wherein R" is an amino acid chain of less than 3 residues.

3. The compound of claim 1 wherein X is CPh$_2$, and R" is glycine.

* * * * *